United States Patent
Ito et al.

(10) Patent No.: US 12,378,287 B2
(45) Date of Patent: Aug. 5, 2025

(54) NOROVIRUS-BINDING PEPTIDE

(71) Applicant: Kao Corporation, Tokyo (JP)

(72) Inventors: Yoshitaka Ito, Sakura (JP); Takuya Morimoto, Tokyo (JP); Shigefumi Kumachi, Saitama (JP); Naoto Nemoto, Saitama (JP)

(73) Assignee: Kao Corporation, Tokyo (JP)

( * ) Notice: Subject to any disclaimer, the term of this patent is extended or adjusted under 35 U.S.C. 154(b) by 923 days.

(21) Appl. No.: 17/613,331

(22) PCT Filed: May 28, 2020

(86) PCT No.: PCT/JP2020/021239
§ 371 (c)(1),
(2) Date: Nov. 22, 2021

(87) PCT Pub. No.: WO2020/241800
PCT Pub. Date: Dec. 3, 2020

(65) Prior Publication Data
US 2022/0227809 A1    Jul. 21, 2022

(30) Foreign Application Priority Data
May 29, 2019    (JP) ................. 2019-100758

(51) Int. Cl.
*C07K 7/06*    (2006.01)
*G01N 33/569*    (2006.01)

(52) U.S. Cl.
CPC ......... *C07K 7/06* (2013.01); *G01N 33/56983* (2013.01); *G01N 2333/085* (2013.01)

(58) Field of Classification Search
None
See application file for complete search history.

(56) References Cited

U.S. PATENT DOCUMENTS

| | | | |
|---|---|---|---|
| 8,124,104 B2 * | 2/2012 | Coit | A61K 39/12 435/325 |
| 2015/0133630 A1 | 5/2015 | Suga et al. | |
| 2016/0061835 A1 | 3/2016 | Palzkill et al. | |
| 2016/0153991 A1 | 6/2016 | Gupta et al. | |
| 2016/0209421 A1 | 7/2016 | Suga | |
| 2019/0002535 A1 * | 1/2019 | Yugawa | G01N 33/56983 |

FOREIGN PATENT DOCUMENTS

| | | |
|---|---|---|
| JP | 2015-42159 A | 3/2015 |
| JP | 2019-043946 A | 3/2019 |
| JP | 2020-196706 A | 12/2020 |

(Continued)

OTHER PUBLICATIONS

International Search Report for PCT/JP2020/021239; I.A. fd May 28, 2020, mailed Aug. 11, 2020, the Japan Patent Office, Tokyo, Japan.

(Continued)

*Primary Examiner* — Agnieszka Boesen
(74) *Attorney, Agent, or Firm* — Sterne, Kessler, Goldstein & Fox P.L.L.C.

(57) ABSTRACT

A peptide that specifically binds to norovirus, which is useful for detection and infection control of norovirus is provided. A norovirus-binding peptide consisting of an amino acid sequence selected from the group consisting of SEQ ID NOs: 1 to 327.

8 Claims, 4 Drawing Sheets

Specification includes a Sequence Listing.

(56) References Cited

FOREIGN PATENT DOCUMENTS

| JP | 2020-196707 A | 12/2020 |
| WO | WO 2013/183707 A1 | 12/2013 |

OTHER PUBLICATIONS

International Preliminary Report on Patentability (IPRP), Chapter I of the Patent Cooperation Treaty, including the Written Opinion, for PCT/JP2020/021239; I.A. fd May 28, 2020, issued Nov. 16, 2021, by the International Bureau of WIPO, Geneva, Switzerland.

Hwang, HJ et al., "High sensitive and selective electrochemical biosensor: Label-free detection of human norovirus using affinity peptide as molecular binder," Biosens Bioelectron. Jan. 15, 2017;87:164-170. doi: 10.1016/j.bios.2016.08.031. Epub Aug. 12, 2016. PMID: 27551996.

Yamaguchi, J et al., "cDNA display: a novel screening method for functional disulfide-rich peptides by solid-phase synthesis and stabilization of mRNA-protein fusions," Nucleic Acids Res. Sep. 2009;37(16):e108. doi: 10.1093/nar/gkp514. Epub Jun. 15, 2009. PMID: 19528071; PMCID: PMC2760808, 13 pages.

Heo, N.S. et al., "Affinity Peptide-guided Plasmonic Biosensor for Detection of Noroviral Protein and Human Norovirus," Biotechnol Bioproc E 24, 318-325 (2019). doi.org/10.1007/s12257-018-0410-6.

Baek SH et al., "Development of a rapid and sensitive electrochemical biosensor for detection of human norovirus via novel specific binding peptides," Biosens Bioelectron. Jan. 1, 2019;123:223-229. doi: 10.1016/j.bios.2018.08.064. Epub Aug. 28, 2018. PMID: 30195404.

Mochizuki Y et al., "A versatile puromycin-linker using cnvK for high-throughput in vitro selection by cDNA display," J Biotechnol. Oct. 20, 2015;212:174-80. doi: 10.1016/j.jbiotec.2015.08.020. Epub Aug. 28, 2015. PMID: 26321074.

\* cited by examiner

[Figure 1]
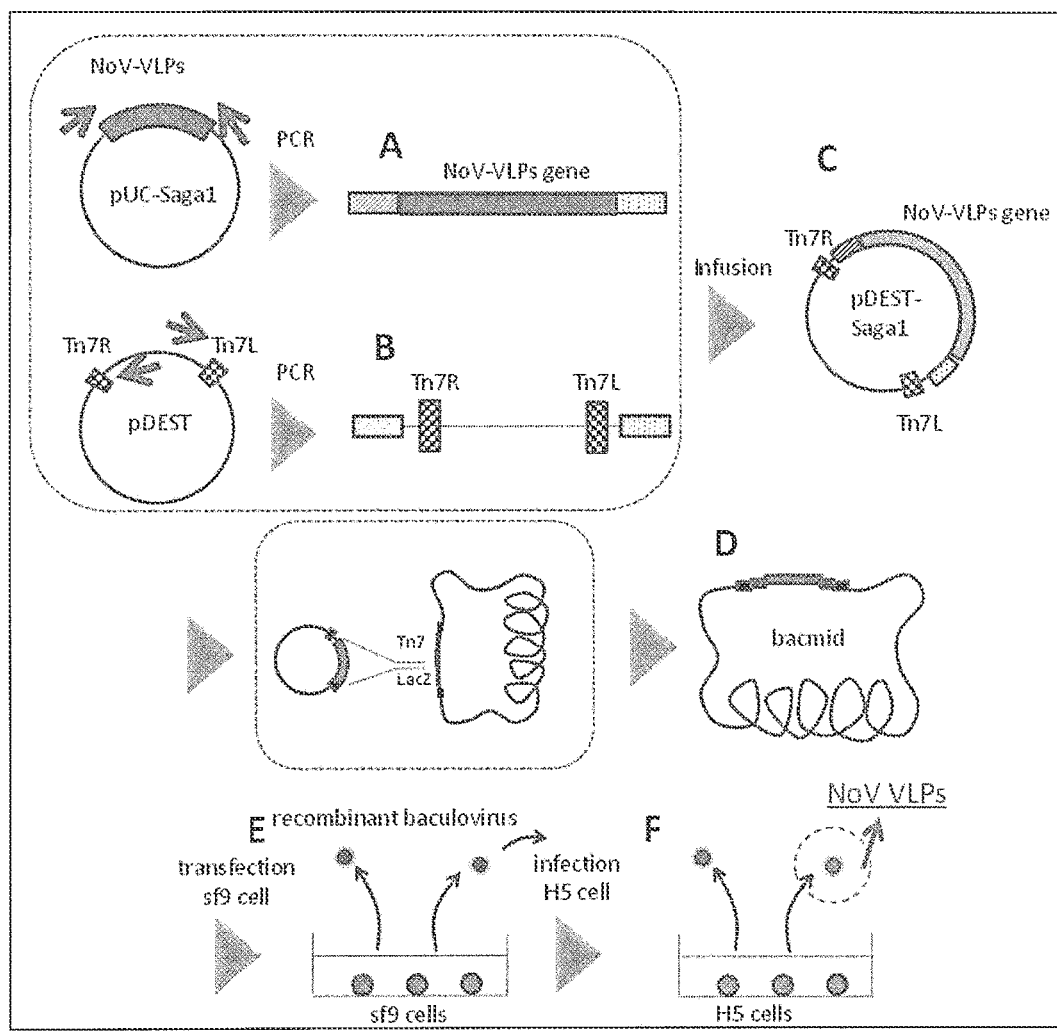

[Figure 2]
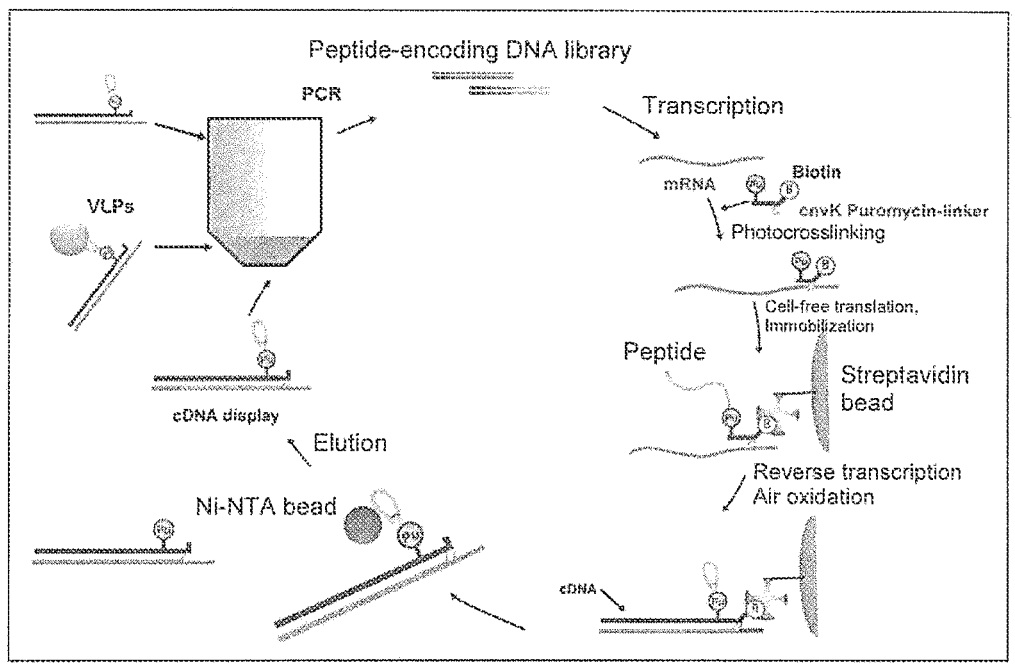

[Figure 3]
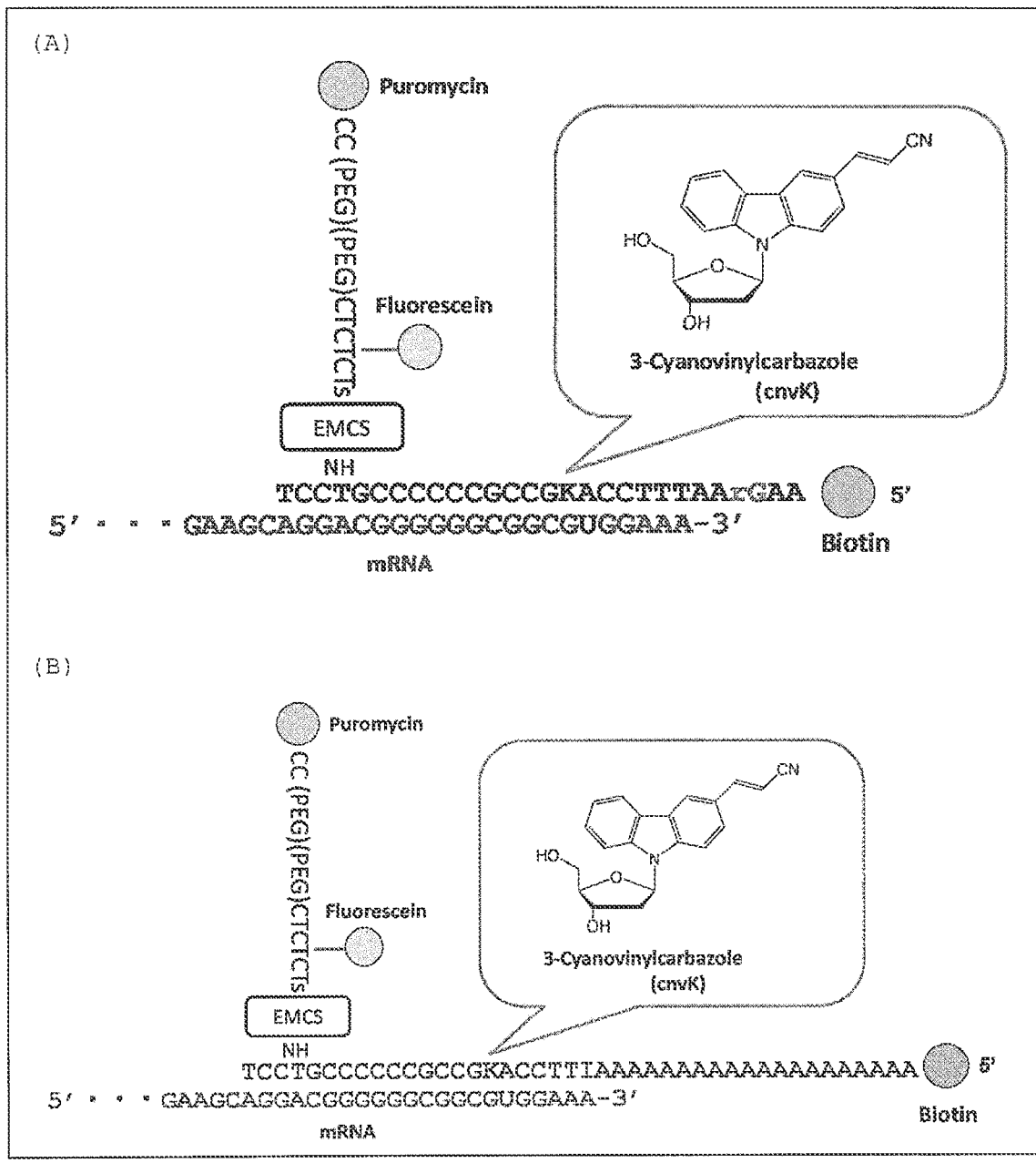

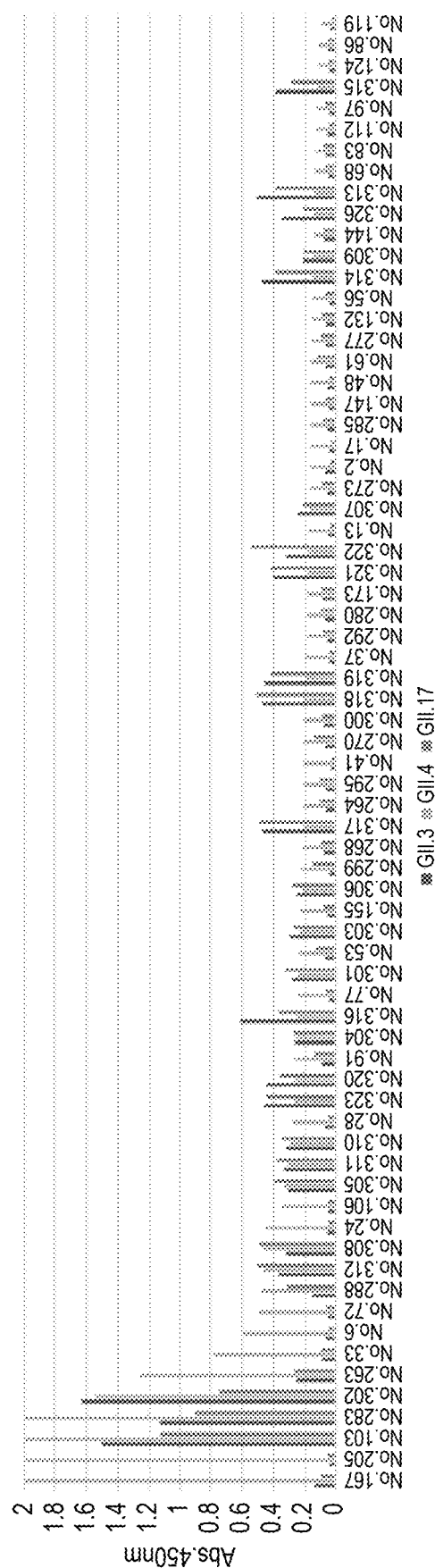
[Figure 4]

NOROVIRUS-BINDING PEPTIDE

FIELD OF THE INVENTION

The present invention relates to a norovirus-binding peptide having affinity to norovirus.

BACKGROUND OF THE INVENTION

Norovirus is a virus that has been called SRSV (Small Round Structured Virus) and also called NLV (Norwalk-like virus), and is classified into five categories from GI (genogroup I) to GV (genogroup V) based on the genotypes, among which GI, GII, and GIV infect humans. Norovirus is a virus that propagates in human intestinal cells and causes food poisoning with symptoms such as diarrhea, vomiting, abdominal pain, nausea, and fever. The main source of infection is food, and raw oysters are often a problem. In addition, in recent years, human to human transmission through excrement etc. of a virus carrier is also increasing.

Currently, as the detection of norovirus, in addition to observation with as electron microscope, there are a method using an antibody and a method of measuring the amount of an amplification product of norovirus RNA. Furthermore, recently, a polypeptide consisting of 18 amino acids that has affinity to norovirus and is useful for detection of norovirus has also been found, but it has been reported that the bonding strength is low compared to previously reported norovirus antibodies (Non Patent Literature 1).

However, a method for detecting RNA requires reverse transcription and an amplification step, and the operation is complicated and takes time and cost. Antibodies also have problems: the specificity is low in some cases; and animals or culture cells are used for producing and manufacturing antibodies, the quality is unstable and the cost is high.

Accordingly, there is a demand for developing a more effective and simpler norovirus-specific detection method and a prophylactic and therapeutic method for norovirus infection.

NON PATENT LITERATURE 1

Hye Jin Hwang, et al., Biosensors and Bioelectronics, 2017, 87, 164-170

SUMMARY OF THE INVENTION

The present invention relates to the following 1) to 4):
1) a norovirus-binding peptide consisting of an amino acid sequence selected from the group consisting of SEQ ID NOs: 1 to 327;
2) a norovirus-binding peptide consisting of an amino acid sequence selected from the group consisting of SEQ ID NOs: 1 to 327 with a cysteine residue added to either or both of an N-terminus and a C-terminus thereof;
3) a method for detecting norovirus comprising using the norovirus-binding peptide of the above 1) or 2); and
4) a norovirus detection kit comprising the norovirus-binding peptide of the above 1) or 2).

BRIEF DESCRIPTION OF THE DRAWINGS

FIG. 1 is a schematic diagram showing a production flow of VLPs.

FIG. 2 is a schematic diagram showing an outline of screening for norovirus-binding peptides.

FIG. 3 is a schematic diagram showing mRNA-linker conjugates (A: for selection, B: for analysis).

FIG. 4 shows results of evaluation of interaction by ELISA.

DETAILED DESCRIPTION OF THE INVENTION

The present invention relates to provision of a peptide that specifically binds to norovirus, which is useful for specific detection and infection control of norovirus.

The present inventors constructed a cDNA library containing a $10^{14}$-digit number of cDNAs and succeeded in obtaining peptides that specifically bind to norovirus from the library by a cDNA display method, and accomplished the present invention.

According to the present invention, norovirus-binding peptides having high affinity to norovirus are provided. According to the peptides of the present invention, norovirus can be specifically detected with a high sensitivity, and infection of humans with norovirus can be controlled.

The norovirus-binding peptide of the present invention is a peptide composed of 10 amino acids, consisting of an amino acid sequence selected from the Group consisting of SEQ ID NOs: 1 to 327 (Tables 18 to 20).

The peptides have been screened from the cDNA library containing a $10^{14}$-digit number of cDNAs by a cDNA display method through in vitro selection using norovirus as a target molecule and are norovirus-binding peptide aptamers having an ability of specifically binding to norovirus. The peptides are each composed of 10 amino acids of the library sequences consisting of 27.6% of hydrophobic amino acids and 72.4% of hydrophilic amino acids. The norovirus-binding peptides of the present invention are those that are recognized as a cluster in cluster analysis based on amino acid sequence similarity or that frequently appear among norovirus-binding peptides screened by in vitro selection using norovirus as a target molecule. From the viewpoint of cluster analysis, among clusters with a hamming distance of 5 or less, a norovirus-binding peptide consisting of an amino acid sequence selected from the group consisting of SEQ ID NOs: 6 to 10, 21 to 25, 31 to 35, 71 to 75, 101 to 110, 164 to 172, and 205 to 260 is preferred, and among clusters with a q-gram distance divided into 3-character strings of 4 or less and including 3 or more sequences, a norovirus-binding peptide consisting of an amino acid sequence selected from the group consisting of SEQ ID NOs: 261 to 263, 282 to 284, and 288 to 290 is preferred. From the viewpoint of the appearance frequency of a norovirus-binding peptide, a norovirus-binding peptide consisting of any of amino acid sequences of SEQ ID NOs: 301, 302, 305, 308, 310 to 312, 316, 317, 320, and 323 is preferred.

Furthermore, among these sequence groups, a norovirus-binding peptide consisting of an amino acid sequence selected from the group consisting of SEQ ID NOs: 101 to 105, 164 to 172, 205 to 260, 261 to 263, 282 to 284, 288 to 290, and 302 is more preferred, and a norovirus-binding peptide consisting of an amino acid sequence selected from the group consisting of SEQ ID NOs: 103, 167, 205, 263, 283, 288, and 302 is particularly preferred.

The peptide of the present invention encompasses, as an aspect, a peptide consisting of an amino acid sequence selected from the group consisting of SEQ ID NOs: 1 to 327 with a cysteine residue added to either or both of an N-terminus and a C-terminus thereof. The peptide having cysteine residues at both terminuses can form a cyclic peptide through a disulfide bond of the cysteine residues.

In addition, the peptide of the present invention encompasses, as another aspect, a peptide consisting of an amino acid sequence selected from the group consisting of SEQ ID NOs: 1 to 327, or an amino acid sequence selected from the group consisting of SEQ ID NOs: 1 to 327 with a cysteine residue added to either or both of the N-terminus and the C-terminus thereof, wherein arbitrary 1 to 20 amino acid residues are further added to either or both of the N-terminus and the C-terminus of the peptide, as long as the ability of specifically binding with norovirus is maintained.

Viruses that belong to norovirus infecting humans are classified into three gene groups of Genogroup I (GI), Genogroup II (GII), and Genogroup IV (GIV) at present, and 90% or more of reported infection cases are in the GII group. It is inferred there is a serotype corresponding to each genotype. In the present invention, the norovirus encompasses viruses belonging to such norovirus. Empty virus-like particles (VLPs) that are extremely similar to virus particles can be produced by incorporating the structural protein region of a norovirus genome into baculovirus and expressing it in insect cells. The VLPs have the structure of norovirus itself and has antigenicity equivalent to that of virus particles, but do not have the genomic RNA therein, being empty and not having infectivity. Accordingly, in the present invention, norovirus encompasses such VLPs.

Examples of the VLPs include VLPs produced using the norovirus genome, such as a GII.4 Sagal strain (Genbank No. AB447456), a GII.4 Sydney strain (Genbank No. JX459908.1), a GII.3 TCH strain (Genbank No. KF006265), a GII.2 Ehime strain (Genbank No. LC145808), a GII.17 Kawasaki strain (Genbank No. AB983218), and a GII.17 Saitama strain (Genbank No. KJ196286.1).

The peptide of the present invention can be produced using norovirus (empty virus-like particles: VLPs) as a target molecule by in vitro evolution method known in the art, for example, by a cDNA display method (Nucleic cid Research, vol. 37, No. 16, e108 (2009)). That is, the peptide can be produced by constructing a cDNA library containing cDNAs (library of peptide-linker-mRNA/cDNA conjugates) and subjecting it to in vitro selection by a cDNA display method.

Specifically, the peptide can be produced by the following steps a) to c) (see FIG. 2):
a) a step of preparing DNA fragments (construct) encoding a desired random peptide library;
b) a cDNA display-producing step of producing peptide-linker-mRNA/cDNA in vitro with a cDNA display method using the construct prepared in the above step; and
c) a selection step of mixing the cDNA displays obtained in the above step with VLPs, collecting the cDNA displays bound to the VLPs, and screening for VLP-bound cDNA displays.

a. Step of Preparing Construct

As a construct for producing a norovirus-binding peptide, DNA fragments including a primer region, a promoter region, an untranslated region, a random region, and a tag region from the 5' end toward the 3' end and encoding a desired random peptide library are constructed. Here, the DNA sequence used as the primer region may be a commercially available general one. As the promoter region, for example, T7 or SP6 can be used. As the untranslated region, for example, an Ω region can be used.

For the random region, the DNA is constituted such that hydrophobic amino acids of alanine, valine, leucine, isoleucine, methionine, proline, phenylalanine, and tryptophan is 27.6%, polar amino acids of glycine, serine, threonine, asparagine, glutamine, tyrosine, and cysteine is 36.0%, basic amino acids of lysine, arginine, and histidine is 18.4%, and acidic amino acids of aspartic acid and glutamic acid is 12.0%.

b. cDNA Display-Producing Step

The production of cDNA display includes, as shown in FIG. 2, a mRNA preparation step (b1), a linker-mRNA conjugate formation step (b2), a peptide-linker-mRNA conjugate formation step (b3), a particle-binding step (b4), a cDNA display formation step (b5), a peptide crosslinking step (b6), and a cDNA display release step (b7).

In the mRNA preparation step (b1), mRNA is prepared from the above-described construct by transcription. Then, in (b2), a linker-mRNA conjugate is formed by binding the mRNA obtained in the mRNA preparation step to a linker to which puromycin is bound.

Subsequently, in (b3), a peptide-linker-mRNA conjugate is formed by binding a peptide having an amino acid sequence corresponding to the mRNA sequence translated by a cell-free translation system to puromycin.

Subsequently, in the particle-binding step (b4), the peptide-linker-mRNA conjugate obtained as in above is bound to magnetic particles.

Subsequently, in (b5), the mRNA of the peptide-linker-mRNA conjugate bound to the magnetic particles is reversely transcribed to form cDNA to obtain peptide-linker-mRNA/cDNA. ("cDNA display").

Subsequently, in (b6), cysteines on the N-terminus and the C-terminus of the random region of the peptide in the cDNA display obtained in the above step are crosslinked by a crosslinking reaction.

Subsequently, in the complex release step (b7), the cDNA display obtained in the above step is released from the magnetic particles and is purified as needed.

c. Selection Step of VLP-Bound cDNA Displays

The selection of VLP-bound cDNA displays includes a solution addition step (c1), a separation step (c2), and a collection step (c3).

In the solution addition step (c1), a cDNA display-containing solution is added to a VLP solution. Continuously, in the separation step (c2), the mixture solution of the VLP and cDNA display solutions is subjected to, for example, centrifugation at 130,000×g for 5 minutes to precipitate the VLPs. Thus, the cDNA display not bound to the VLPs is separated. Subsequently, in the collection step (c3), the cDNA display bound to the VLPs is collected together with the VLPs.

The peptide of the present invention can be selected from a predetermined DNA library in vitro as described above.

In addition, the peptide of the present invention can be produced by a known method for manufacturing a peptide, for example, by a chemical synthesis method, such as a liquid-phase method, a solid-phase method, or a hybrid method of a liquid-phase method and a solid-phase method; or a genetic recombination method.

Since the peptide of the present invention specifically binds to norovirus, it is possible to verify that norovirus is present or not present in a sample by bringing the peptide into contact with the sample that contains or may contain norovirus.

That is, for example, norovirus in a sample can be detected using the peptide of the present invention instead of an anti-norovirus antibody in an immunoassay, such as an ELISA method.

The peptide of the present invention when used as a detection reagent may be labeled to be detectable. In labeling of the peptide, for example, not only enzymes, such as peroxidase and alkaline phosphatase, but also radioactive materials, fluorescent materials, luminescent materials, etc. are used. In addition, nanoparticles, such as colloidal gold and quantum dots, can also be used. In an immunoassay, the peptide of the present invention can also be detected by labeling the peptide with biotin and binding avidin or streptavidin labeled with an enzyme or the like thereto.

Among the immunoassays, an ELISA method using an enzyme label is preferred in the point that it can simply and rapidly measure an antigen. When norovirus is detected by an ELISA method using the peptide of the present invention, for example, norovirus is immobilized on a solid support, and a peptide previously labeled with biotin is bound thereto. After washing, an avidin-modified enzyme is allowed to bind to the biotin and is then allowed to react with an enzyme substrate to cause color development, and the norovirus can be detected by measuring the absorbance. Alternatively, the peptide of the present invention is solid-phased, and norovirus is bound thereto. After washing, an anti-norovirus antibody labeled with an enzyme or an anti-norovirus antibody and an enzyme-labeled secondary antibody is allowed to bind thereto, and the norovirus can be detected by reacting an enzyme substrate to cause color development and measuring the absorbance.

As the enzyme substrate, when the enzyme is alkaline phosphatase, for example, p-nitrophenyl phosphate (NPP) can be used, and when the enzyme is peroxidase, for example, 3,3',5,5'-tetramethylbenzidine can be used. As the solid support, an insoluble support in a shape of, for example, a bead, microplate, test tube, stick, or test piece made of a material such as polystyrene, polycarbonate, polyvinyl toluene, polypropylene, polyethylene, polyvinyl chloride, nylon, polymethacrylate, latex, gelatin, agarose, cellulose, Sepharose, glass, metal, ceramic, or a magnetic material, can be used. Immobilization of the peptide of the present invention and so on to the solid support can be performed by binding through a known method such as a physical adsorption method, a chemical bond method, or a method of simultaneously performing these methods.

The peptide of the present invention can be a component of a norovirus detection kit. The detection kit can include, in addition to the peptide of the present invention, a reagent and an instrument necessary for detection such as an antibody, a solid support, a buffer solution, an enzyme reaction stopping solution, and a microplate reader.

The sample that is an object of the detection kit is not particularly limited as long as, for example, the sample contains or may contain norovirus, and examples thereof include clinical materials such as feces and vomit collected from a patient, a separated virus culture solution, food such as oyster, and tap and sewage water.

The peptide of the present invention can specifically bind to, for example, the capsid protein of norovirus to inhibit the binding of the virus to a cell. Accordingly, the peptide of the present invention can be used as an anti-norovirus formulation or a medicine for preventing or treating norovirus.

When the peptide of the present invention is used as a medicine, it may be an oral form or a parenteral form and can be appropriately used in combination with known pharmaceutically acceptable avirulent carrier and diluent. Although typical examples of the parenteral administration include an injection, the peptide can also be administered by inhalation with a spray agent, etc.

Regarding the above-described embodiments, the present invention discloses the following aspects:

<1> a norovirus-binding peptide consisting of an amino acid sequence selected from the group consisting of SEQ ID NOs: 1 to 327;

<2> a norovirus-binding peptide consisting of an amino acid sequence selected from the group consisting of SEQ ID NOs: 1 to 327 with a cysteine residue bound to either or both of the N-terminus and the C-terminus thereof;

<3> the norovirus-binding peptide of <2>, wherein the cysteine residue is bound to the N-terminus and the C-terminus of the amino acid sequence selected from the group consisting of SEQ ID NOs: 1 to 327;

<4> the norovirus-binding peptide of <3>, wherein the cysteine residue bound to the N-terminus and the cysteine residue bound to the C-terminus of the peptide consisting of an amino acid sequence selected from the group consisting of SEQ ID NOs: 1 to 327 are linked to each other via a disulfide bond to form a ring;

<5> a norovirus-binding peptide consisting of an amino acid sequence of the peptide according to any one of <1> to <4> with 1 to 20 amino acids bound to either or both of the N-terminus and the C-terminus of the peptide;

<6> a method for detecting norovirus using the norovirus-binding peptide according to any one of <1> to <5>;

<7> a norovirus detection kit comprising the norovirus-binding peptide according to any one of <1> to <5>;

<8> the norovirus-binding peptide according to any one of <1> to <6> or the norovirus detection kit according to <7>, wherein the amino acid sequence selected from the group consisting of SEQ ID NOs: 1 to 327 is an amino acid sequence selected from the group consisting of SEQ ID NOs: 6 to 10, 21 to 25, 31 to 35, 71 to 75, 101 to 110, 164 to 172, 205 to 263, 282 to 284, 288 to 290, 301, 302, 305, 308, 310 to 312, 316, 317, 320, and 323;

<9> the norovirus-binding peptide according to any one of <1> to <6> or the norovirus detection kit according to <7>, wherein the amino acid sequence selected from the Group consisting of SEQ ID NOs: 1 to 327 is an amino acid sequence selected from the group consisting of SEQ ID NOs: 101 to 105, 164 to 172, 205 to 260, 261 to 263, 282 to 284, 288 to 290, and 302; and <10> the norovirus-binding peptide according to any one of <1> to <6> or the norovirus detection kit according to <7>, wherein the amino acid sequence selected from the Group consisting of SEQ ID NOs: 1 to 327 is an amino acid sequence selected from the group consisting of SEQ ID NOs: 103, 167, 205, 263, 283, 288, and 302.

EXAMPLES

The present invention will now be more specifically described by examples.

Reference Example: Production of VLPs (1) Introduction of VP1 and VP2 Genes Into pDEST8

Artificial synthesis of DNAs encoding the VP1 and VP2 regions, which are structural protein regions, of the GII.4 Sagal strain (Genbank No: AB447456), the GII.3 TCH strain (Genbank No. KF006265), and the GII.17 Saitama strain (Genbank No. KJ196286.1) of norovirus (hereinafter, may be abbreviated to NoV), was outsourced to Fasmac Co., Ltd., and a target gene was introduced therein using the position of the slash of 5'-CAGACGTGTGCTCTTCC-GATCTGAT/ATCAGATCGGAAGAGCGTCGTTAAG-3' (SEQ ID NO: 328), which is the lacZ-α region of pUCFa plasmid, as the cloning site. In GII.4, a PCR reaction was performed using a synthesized pUC-Sag1 (FIG. 1) DNA as a template and using primer 1 (5'-CATCACAAGTTTGTA-CAAAAAAGCAGGCTGTGA-3': SEQ ID NO: 329) and primer 2 (5'-TATCACCACTTTGTA-CAAGAAAGCTGGGTT-3': SEQ ID NO: 330) to obtain a fragment (FIG. 1-A). In GII.3, a PCR reaction was performed using a synthesized pUC-TCH DNA as a template and using primer 3 (5'-ATCACAAGTTTGTACTGG-GAGGGCGATCGCA-3': SEQ ID NO: 331) and primer 4 (5'-CTATCACCACTTTGTTCGCTACCTCGCGAA-3': SEQ ID NO: 332) to obtain a fragment (FIG. 1-A). In addition, a PCR reaction was performed using a pDEST8 plasmid (Invitrogen) as a template and using primer 5 (5'-ACAAGTGGTGATAGCTTGTCGAGAAGTA-3': SEQ ID NO: 333) and primer 6 (5'-GTACAAACTTGTGAT-GATCCGCGCCCGAT-3': SEQ ID NO: 334) to obtain a fragment (FIG. 1-B). The resulting PCR fragment A and fragment B were mixed and were reacted to each other using an InFusion HD Cloning Kit (Clontech Laboratories, Inc.), and using 1 ng of the resulting DNA (FIG. 1-C), Competent Quick DH5α (manufactured by TOYOBO CO., LTD.) was transformed. Selection was performed with an LB agar plate culture medium containing 100 μg/mL of ampicillin, the resulting colonies were cultured in an LB liquid culture medium containing 100 μg/mL of ampicillin, and the plasmid was extracted from the resulting cells using a QIAprep Spin Miniprep Kit (manufactured by QIAGEN N.V.). The sequence of the resulting plasmid having NoV gene introduced was determined using a DNA sequencer to verify that the target sequence was inserted.

In GII.17, a sequence in which an attL1 sequence (5'-ccccaaataatgattttattttgactgatagtgacctgttcgttgcaacaaattgat gagcaatgcttttttataatgccaactttgtacaaaaaagcaggct-3': SEQ ID NO: 335) was introduced to 4 nucleotides upstream from the start codon of the VP1 region and a polyadenine sequence of 30 adenines followed by an attL2 sequence (5'-agct-tacccagctttcttgtacaaagttggcattataagaaagcattgcttatcaat ttgttgcaacgaacaggtcactatcagtcaaaataaaatcattatttg-3': SEQ ID NO: 336) were introduced to 55 nucleotides downstream from the termination codon of the VP2 region was artificially synthesized. The resulting pUC-Saitama and pDEST8 were mixed in equal amounts, and were mixed as shown in Table 1, followed by a reaction at 25° C. for 1 hour. After the reaction, 1 L of proteinase K (manufactured by Takara Bio Inc.) was added thereto, followed by a reaction at 37° C. for 10 minutes. Using 1 ng of the reaction solution, Competent Quick DH5α (manufactured by TOYOBO CO., LTD.) was transformed, and selection was performed with an LB agar plate culture medium containing 100 μg/mL of ampicillin. The resulting colonies were cultured in an LB liquid culture medium containing 100 μg/mL of ampicillin, and pDEST8 encoding GII.17 was purified and obtained from the resulting cells using a QIAprep Spin Miniprep Kit (manufactured by QIAGEN N.V.).

TABLE 1

| Composition | Content |
| --- | --- |
| pUC-Saitama | 0.75 μL (150 ng) |
| pDEST8 (manufactured by Invitrogen) | 1.0 μL (150 ng) |
| UltraPure Water (manufactured by Invitrogen) | 6.25 μL |
| BP clonase (manufactured by Thermo Fisher Scientific) | 2 μL |

(2) Introduction of VP1 and VP2 Genes Into bMON14272 Bacmid (Manufactured by Invitrogen)

The obtained plasmid was introduced into Bacmid according to the protocol attached to the product by the following method (FIG. 1-D).

NoV VP1 and VP2 regions were introduced into bMON14272 bacmid (manufactured by Invitrogen) using the obtained plasmid having Nov gene introduced and MAX Efficiency DH10Bac Competent Cells (manufactured by Invitrogen) (FIG. 1-D). Whether each gene was introduced into bacmid or not was verified by performing selection in an LB culture medium containing 40 μg/mL of IPTG (isopropyl β-D-1-thiogalactopyranoside: manufactured by FUJIFILM Wako Pure Chemical Corporation), 100 μg/mL of X-Gal (5-bromo-4-chloro-3-indolyl β-D-galactopyranoside: manufactured by FUJIFILM Wako Pure Chemical Corporation), 50 μg/mL of kanamycin, 7 μg/mL of gentamicin, and 10 μg/mL of tetracycline (kanamycin resistance gene, tetracycline resistance gene, and gentamicin resistance gene were encoded in bMON14272, helper plasmid present in DH10Bac Competent Cell, and the region of pDEST to be inserted into bacmid, respectively), and further whether each fragment was inserted into a target side or not was verified by color selection. The obtained white colonies were cultured in an LB liquid culture medium containing 50 μg/mL of kanamycin, 7 μg/mL of gentamicin, and 10 μg/mL of tetracycline, and bacmid was extracted from the resulting cells using a QIAprep Spin Mini prep Kit (manufacture by QIAGEN N.V.). The concentration of the extracted DNA solution was verified with NanoDrop (manufactured by Thermo Fisher Scientific).

(3) Production of Recombinant Baculovirus (rBV) by Transfection of Bacmid Having NoV VP1 and VP2 Introduced Bacmid into which NoV VP1 and VP2 genes were introduced was transfected into Sf9 cells (manufactured by Invitrogen) using a Lipofecctamine LTX Reagent & Plus Reagent (manufactured by Invitrogen) according to the protocol attached thereto (FIG. 1-E). The transfected cells were cultured using an Sf900III (manufactured by Invitrogen) culture medium at 27° C. for 1 week. After the culture, the culture medium was centrifuged, and the supernatant was collected to obtain recombinant baculovirus (rBV) including the NoV gene.

(4) Production of Nov VLP by Infection With rBV

The rBV was added at $1.0 \times 10^7$ pfu/mL to $1.0 \times 10^7$ cells/flask of High Five cells (manufactured by Invitrogen) to cause infection at an MOI of 2, and the cells were cultured using an Express five (manufactured by Invitrogen) culture medium at 27° C. (FIG. 1-F). After 7 days from the infection, the culture supernatant was collected by centrifugation. The recovered supernatant was further centrifuged at 10,000×g for 1 hour to pellet down the baculovirus, and the cell supernatant was collected. The collected supernatant containing NoV VLP was further centrifuged with an SW32Ti rotor (manufactured by Beckman Coulter, Inc.) at 32,000 rpm for 2 hours to pellet down the NoV VLP. The pellet separated from the supernatant was dissolved in an Express five culture medium containing 1.9 mg of CsCl (for density gradient centrifugation, manufactured by FUJIFILM Wako Pure Chemical Corporation) and centrifuged using SW55Ti (Manufactured by Beckman Coulter, Inc.) at 40,000 rpm for 20 hours for separation and purification, and a fraction visually observed by irradiation with white light was collected. The collected fraction was centrifuged again with the SW32Ti rotor at 32,000 rpm for pellet down, the supernatant was removed, and the pellet was suspended in 500 µL of an Express five culture medium. The VLP concentration was quantitatively measured by a Bradford method. As a standard protein, BSA (manufactured by FUJIFILM Wako Pure Chemical Corporation) was used.

Example 1: Manufacturing of Norovirus-Binding Peptide (See FIG. 2)

(1) Construction of DNA Library

A DNA library was designed such that the peptide library is composed of peptides having a length of 10 amino acids.

Nucleotide Sequence of DNA Library

[SEQ ID NO: 337]
5'-
GATCCCGCGAAATTAATACGACTCACTATAGGGGAAGTATTTTTACAACA

ATTACCAACAACAACAACAAACAACAACAACATTACATTTTACATTCTAC

AACTACAAGCCACCATGGGCTGCQRSQRSQRsQRSQRSQRSQRSQRS

QRSTGCGGGGAGGCAGCCATCATCATCATCATCACGGCGGAAGCAGGAC

GGGGGGCGGCGTGGAAA-3'

TABLE 2

Each sequence included in template DNA and position thereof

| Nucleotide Position | Region Name |
| --- | --- |
| 14 to 33 | T7 promoter |
| 34 to 36 | 5' cap |
| 37 to 107 | Ω sequence |
| 110 to 114 | Kozak sequence |
| 115 to 120 | MG |
| 121 to 156 | Cys-library sequence-Cys |
| 157 to 168 | GGGS |
| 169 to 186 | Hexahistidine tag |
| 187 to 195 | GGS |
| 196 to 217 | Hybridization region for linker DNA |

The above-mentioned DNA library was constructed by binding three DNA sequence fragments, a T7-PRO-Ω region (SEQ ID NO: 338), a random region (SEQ ID NO: 339), and a His-Y tag region (SEQ ID NO: 340), by extension PCR. This library was designed such that cysteines appear on the N-terminus and the C-terminus of the random region. The random region, the His-Y tag region, and the T7-PRO-Ω region were obtained by outsourcing the respective DNA synthesis to TSUKUBA OLIGO SERVICE CO. LTD. The following extension PCR was performed using them to construct the above DNA library.

[SEQ ID NO: 338]
5'
GATCCCGCGAAATTAATACGACTCACTATAGGGGAAGTATTTTTACAACA

ATTACCAACAACAACAACAAACAACAACAACATTACATTTTACATTCTAC

AACTACAAGCCACCATG 3'

[SEQ ID NO: 339]
5'-
ACAACTACAAGCCACCATGGGCTGCQRSQRSQRSQRSQRSQRSQRSQ

RSQRSTGCGGGGGAGGCAGCCATCATCA-3'

In the sequences above, the ratios of appearance frequency of nucleotides (A:T:G:C) other than ATCG are as follows:

Q: A=0.1, T=0.2, G=0.3, C=0.4,
R: A=0.4, T=0.1, G=0.3, C=0.2, and
S: A=0.4, T=0.2, G=0.2, C=0.2.

[SEQ ID NO: 340]
5'
TTTCCACGCCGCCCCCCGTCCTGCTTCCGCCGTGATGATGATGATGATGG

CTGCCTCCCCC 3'

In the extension PCR of the first stage of synthesis, a reaction solution having the composition shown in the following Table 3 was prepared to 50 µL with ultrapure water, and a DNA fragment including the random region and the His-Y tag region bound to each other was amplified by the following PCR program. The PCR program included (a) 96° C. (2 min), (b) 94° C. (20 sec), (c) 69° C. (5 sec), (d) 72° C. (20 sec), and (e) 72° C. (2 min), and the steps (b) to (d) were repeated 5 cycles.

TABLE 3

| Composition | Content (µL) |
| --- | --- |
| Random region (10 pmol/µL) | 1 |
| His-Y tag region (10 pmol/µL) | 1 |
| 5× PrimeSTAR Buffer (manufactured by Takara Bio Inc.) | 10 |
| dNTP mixture (25 mM each) (manufactured by Takara Bio Inc) | 4 |
| TaKaRa PrimeSTAR (manufactured by Takara Bio Inc.) | 0.5 |

In the extension PCR of the second stage, a reaction solution having the composition shown in the following Table 4 was prepared to 50 µL with ultrapure water, the T7-PRO-SD region was extended by the following PCR program to amplify the DNA library. The PCR program included (a) 96° C. (2 min), (b) 94° C. (20 sec), (c) 59° C. (5 sec), (d) 72° C. (30 sec), and (e) 72° C. (2 min), and the steps (b) to (d) were repeated 15 cycles. Subsequently, the DNA library was purified by polyacrylamide gel electrophoresis (PAGE).

TABLE 4

| Composition | Content (µL) |
|---|---|
| Extended PCR product in first stage (0.5 pmol/µL) | 10 |
| T7-PRO-Ω region (10 pmol/µL) | 5 |
| 5× PrimeSTAR Buffer (manufactured by Takara Bio Inc.) | 10 |
| dNTP mixture (25 mM each (manufactured by Takara Bio Inc.) | 4 |
| TaKaRa PrimeSTAR (manufactured by Takara Bio Inc.) | 0.25 |

(2) Transcription of DNA Library

Transcription of the DNA library was performed using RiboMAX Large Scale RNA Production Systems-T7 (manufactured by Promega Corporation) according to the protocol attached thereto. The reaction scale was 20 µL using 1 µg of the DNA library. The mRNA obtained by the transcription reaction was purified using an After Tri-Reagent RNA Clean-Up Kit (manufactured by FAVORGEN Biotech Corporation).

Subsequently, the obtained mRNA was ligated to a puromycin linker described later as follows (FIG. 3(A)). Firstly, 20 pmol of each of a puromycin linker and the mRNA, 4 µL of 0.25 M Tris-HCl (pH 7.5), and 4 µL of 1 M NaCl were mixed, and the mixture was diluted to 20 µl with ultrapure water. The reaction solution was incubated at 90° C. for 2 minutes and at 70° C. for 1 minute, was then cooled to 4° C., and was then annealed at 25° C. for 1 hour. Subsequently, crosslinking with the puromycin linker was performed using a CL-1000 Ultraviolet Crosslinker by irradiation with ultraviolet light having a wavelength of 365 nm under a condition of 405 mJ/cm$^2$.

DNA of Puromycin Linker

Puromycin linker DNA 1 (FIG. 3(A)) was synthesized by chemical crosslinking of two segments (puromycin segment (PS) and a short biotin segment (SBS) using EMCS (N-(6-maleimidocaproyloxy)succinimide: manufactured by DOJINDO LABORATORIES). The linker used was that described in the literature (Mochizuki Y., Suzuki T., Fujimoto K., Nemoto N. (2015), A versatile puromycin-linker using cnvK for high-throughput in vitro selection by cDNA display, J. Biotechnol., 212, 174-80).

The sequence structure of the puromycin segment (PS) is shown below:

5'-(S)-TCTCTC(F)-(PEG) (PEG)-CC-(Puro)-3'.

Here, (S) represents 5'-thiol-modifier C6 (compound name: S-trityl-6-mercaptohexyl-1-[(2-cyanoethyl)-(N,N-diisopropyl)]-phosphoramidite, manufactured by Glen research), and (F) represents fluoresceine-dT. (Puro) represents puromycin CPG (5'-dimethoxytrityl-N-trifluoroacetyl-puromycin, 2'-succinoyl-long chain alkylamino-CPG, manufactured by Glen research).

The sequence structure of the short biotin segment (SBS) is then shown below:

(SEQ ID NO: 341)
5'(B)-AA-(rG)-AATTTCCA(K)GCCGCCCCCG(Y)CCT-3'.

Here, (Y) represents amino-modifier C6 deoxythymine (5'-dimethoxytrityl-5-[N-(trifluoroacetylaminohexyl)-3-acrylimido]-2'-deoxyuridine, 3'-[(2-cyanoethyl)-(N,N-diisopropyl)]-phosphoramidite, manufactured by Glen research), (K) represents 3-cyanovinylcarbazole (cnvK), (B) represents biotin-triethylene glycol (TEG), manufactured by Glen research), and (rG) represents riboguanine (manufactured by Glen research). Synthesis of PS and SES was outsourced to TSUKUBA OLIGO SERVICE CO. LTD. and was performed according to a usual method.

The 5'-thiol group of the PS was reduced with 1 mM tris(2-carboxyethyl)phosphine hydrochloride (TCEP: manufactured by Thermo Fisher Scientific) in 100 µL of a 50 mM phosphate buffer (pH 7.0) at room temperature for 6 hours, and desalted with a NAP-5 column (manufactured by GE Healthcare) at the time of use. A biotin loop in a total amount of 10 nmol and EMCS in a total amount of 2 µmol were added to 100 µL of a 0.2 M sodium phosphate buffer (pH 7.0). Subsequently, the mixture was incubated at 37° C. for 30 minutes, and ethanol precipitation was performed at 4° C. to remove excess EMCS.

This precipitate was washed twice with 500 µL of 70% ethanol cooled in advance in an ice bath and was dissolved in 10 µL of a 0.2 M sodium phosphate buffer (pH 7.0) cooled in advance. The reduced PS was immediately added thereto, followed by stirring at 4° C. overnight. After addition of 4 mM TCEP, incubation was performed at 37° C. for 15 minutes to stop this reaction. Subsequently, ethanol precipitation was performed to remove excess PS at room temperature. In order to remove the biotin loop and uncrosslinked biotin loop-EMCS complex, the precipitate was dissolved in a 0.1 M TEAA (triethylamine acetate: manufactured by Glen research) or phosphate buffer and was purified using a C18 HPLC column under the following condition:

Column: AR-300, 4.6×250 mm (manufactured by NACALAI TESQUE, INC.); solvent: A.: 0.1 M TEAA, solvent B: acetonitrile/water (80:20, v/v) gradient, B/A (15 to 35%, 33 min); flow rate: 0.5 mL/min; and detection wavelength: absorbance 254 nm and 490 nm.

Fractions from the final peak at absorbance 254 nm (corresponding to a single peak at absorbance 490 nm) were collected. After drying, the fractions were resuspended in water treated with diethylpyrocarbonate (DEPC) and were stored. As described above, puromycin linker DNA 1 could be obtained.

Binding of mRNA and Puromycin Linker DNA 1

To 20 pmol of the mRNA obtained by transcription, 20 pmol of the puromycin linker DNA 1, 4 µL of 0.25 M Tris-HCl (pH 7.5), and 4 µL of 1 M NaCl were added, and prepared to 20 µL in total with nuclease-free water (Table 5). Incubation was performed at 90° C. for 1 minute and then at 70° C. for 1 minute, and the temperature was then lowered to 25° C. at a rate of 0.04° C./s. The cnvK and uracil in the mRNA were covalently bonded by irradiation with 405 mJ of ultraviolet light (365 nm) to form a mRNA-linker conjugate. The amount synthesized here was that required in each round.

TABLE 5

Composition for binding of mRNA and puromycin linker DNA

| Composition | Content |
|---|---|
| Puromycin linker DNA 1 | 20 pmol |
| mRNA | 20 pmol |

TABLE 5-continued

Composition for binding of mRNA and puromycin linker DNA

| Composition | Content |
|---|---|
| 0.25M Tris-HCl (pH 7.5) | 4 µL |
| 1M NaCl | 4 µL |

Translation

The mRNA-linker conjugate was translated by a cell-free translation system as follows. A reaction solution having the composition ratio shown in the following Table 6 was prepared to 50 µL with ultrapure water and was reacted at 37° C. for 15 minutes, and 24 µL of 3 M KCl and 6 µL of 1 M $MgCl_2$ were added to this reaction solution. Subsequently, this solution was further reacted at 37° C. for 20 minutes to bind between the C-terminus of the translated peptide and puromycin to obtain a mRNA-peptide conjugate.

TABLE 6

| Composition | Content |
|---|---|
| Rabbit reticulocyte lysate, nuclease treated (manufactured by Promega Corporation) | 35 µL |
| Amino acid mixture minus leucine, 1 mM (manufactured by Promega Corporation) | 0.5 µL |
| Amino acid mixture minus cysteine, 1 mM (manufactured by Promega Corporation) | 0.5 µL |
| mRNA/linker ligation product | 6 pmol |

(3) Purification by Magnetic Beads

Streptavidin (SA) magnetic particles (Dynabeads MyOne Streptavidin C1, manufactured by Invitrogen) were washed according to the manual and were put in an Eppendorf tube in an amount required for immobilizing the peptide-linker-mRNA conjugate, followed by leaving to stand on a magnetic stand for 1 minute. Subsequently, the supernatant was removed, followed by resuspension in a solution A (100 mM NaOH, 50 nM NaCl). After tapping for 1 to 2 minutes, the tube was left to stand on a magnetic stand for 1 minute. Subsequently, the same operation was repeated once with the solution A, and the same operation was repeated once with a solution B (100 mM NaCl).

To the peptide-linker-mRNA conjugate, the same amount of 2× binding buffer (20 mM Tris-HCl (pH 8.0), 2 mM EDTA, 2 M NaCl, 0.2% Tween 20, and 500 mM EDTA) was added, and the mixture was incubated together with the streptavidin (SA) magnetic particles at room temperature for 30 minutes. The Eppendorf tube was left to stand on a magnetic stand for 1 minute, and the supernatant was then removed. After addition of 200 µL of 1× binding buffer, tapping was performed for 1 to 2 minutes, and the tube was then left to stand on a magnetic stand for 1 minute, followed by removal of the supernatant. This operation was further repeated twice to immobilize the peptide-linker-mRNA conjugate on the streptavidin (SA) magnetic particles.

(4) Synthesis of cDNA by Reverse Transcription Reaction

A reaction solution of the ratio shown in the following Table 7 was added to the immobilized peptide-linker-mRNA conjugate in the same volume as that of the streptavidin (SA) magnetic particles, and incubation was performed at 42° C. for 30 minutes for reverse transcription to prepare cDNA display in the state that the conjugate was immobilized on the streptavidin (SA) magnetic particles.

TABLE 7

| Composition | Content (µL) |
|---|---|
| 2.5 mM dNTP MIX (manufactured by Takara Bio Inc.) | 20 |
| 5× RT Buffer (manufactured by TOYOBO CO., LTD.) | 10 |
| Nuclease-free water | 18 |
| ReverTra Ace (manufactured by TOYOBO CO., LTD.) | 2 |

(5) Crosslinking Reaction of Peptide

The cDNA display immobilized on the streptavidin (SA) magnetic beads were washed with a crosslinking buffer (containing 100 mM sodium phosphate (pH 7.4), 0.15 M NaCl, 10 mM EDTA, and 0.025% Tween 20) once, and then 125 µL of a crosslinking buffer containing 10 mM tris(2-carboxyethyl)phosphine hydrochloride (TCEP: manufactured by Thermo Fisher Scientific) and 4 mM bismaleimidoethane (BMOE: manufactured by Thermo Fisher Scientific) was added, followed by incubation at 25° C. for 1 hour to perform crosslinking reaction of the cysteines on the N-terminus and the C-terminus of the random region.

(6) Elution From Purification by Magnetic Beads

The cDNA display immobilized on the streptavidin (SA) magnetic beads was washed with 1×His-tag wash buffer (containing 10 to 30 mM sodium phosphate (pH 7.4), 0.25 to 0.75 M NaCl, 5 to 30 mM imidazole, and 0.025% to 0.1% Tween 20) once, and then. 30 µL of 1×His-tag wash buffer containing 10 U of RNase T1 (manufactured by Ambion, Inc.) was added, followed by incubation at 37° C. for 15 minutes to elute the cDNA display cleaved from the streptavidin (SA) magnetic beads at the cleavage site (ribo G) in the liker.

(7) Purification by Ni-NTA

Ni-NTA magnetic beads (His Mag Sepharose Ni: manufactured by GE Healthcare) were put at 10 µL in an Eppendorf tube, followed by leaving to stand on a magnetic stand for 1 minute. Subsequently, the supernatant was removed, followed by resuspension in 1×His-tag wash buffer. Tapping was performed for 1 to 2 minutes, and the tube was then left to stand on a magnetic stand for 1 minute. This procedure was further repeated once more.

The cDNA display was incubated together with the Ni-NTA magnetic beads at room temperature for 30 minutes. The Eppendorf tube was left to stand on a magnetic stand for 1 minute, and the supernatant was then removed. After addition of 200 µL of 1×His-tag wash buffer, tapping was performed for 1 to 2 minutes, and the tube was then left to stand on a magnetic stand for 1 minute, followed by removal of the supernatant. This operation was further repeated, and 10 µL of a His-tag elution buffer (containing 10 to 30 mM sodium phosphate (pH 7.4), 0.25 to 0.75 M NaCl, 250 to 500 mM imidazole, and 0.025% to 0.1% Tween 20) was then added, followed by incubation at room temperature for 15 minutes to purify the cDNA display.

(8) In Vitro Selection Cycle

The cDNA displays and VLPs were mixed according to the following Table 8 and were prepared to 1 mL with a selection buffer (containing 10 to 30 mM Tris-HCl (pH 7.4) and 0.1 to 0.3 M NaCl), followed by incubation at 25° C. for 30 minutes.

TABLE 8

|    | cDNA display | VLP          |
|----|--------------|--------------|
| R1 | 100 nM       | GII.4 500 nM |
| R2 | 16 nM        | GII.4 50 nM  |
| R3 | 10 nM        | GII.4 25 nM  |
| R4 | 4 nM         | GII.4 25 nM  |
| R5 | 4 nM         | GII.4 20 nM  |
| R6 | 4 nM         | GII.4 10 nM  |
| R7 | 4 nM         | GII.4 10 nM  |

R1 to R7 are the numbers of in vitro selection cycles.

R1 to R7 are the numbers of in vitro selection cycles.

Separation of VLP-cDNA Display Complex by Centrifugation

The above mixture was put in a centrifuge tube and was centrifuged with an ultracentrifuge (CS150FNX, manufactured by Hitachi, Ltd.) at 130,000×g at 4° C. for about 2 hours. The supernatant was removed. The wall surface was washed with 1 mL of a selection buffer, and the supernatant was then removed. The precipitate was redissolved in 100 µL of RNase-free water.

Separation of VLP-cDNA Display Complex by Dialysis

The constructed cDNA display and VLPs were incubated in 100 µL of a dialysis selection buffer (20 mM HEPES (pH 7.4), 150 mM NaCl, and 0.05% Tween 20) at the concentrations shown in Table 9 below at 25° C. for 30 minutes. Subsequently, the resultant was diluted to 1 mL with the dialysis selection buffer, and was put in Float-A-Lyzer G2 Dialysis Device CE, 1000 kD MWCO (manufactured by Spectrum Laboratories, Inc.) and was dialyzed with 1 L of the dialysis selection buffer as the external solution at 25° C. During the dialysis, the external solution was replaced with new one 3 times every 2 hours, and the dialysis was performed overnight (for 8 hours) after the 4th replacement. The dialysis product was concentrated with Amicon Ultra 100K (manufactured by Merck Millipore S.A.S.) at 14,000×g for 5 minutes.

(9) Selection of GII.3 and GII.17 VLP as Objects

To an immunoplate (C-BOTTOM, CLEAR, MICROLON (registered trademark), HIGH BINDING, manufactured by Greiner Bio-One), 100 µL of 3 µg/mL GII.3 or GII.17 VLP solution was added, and immobilization was performed at 4° C. overnight. Subsequently, the solution was discarded, and 200 µL of a blocking agent (END Millipore™ Blok™ NSB Blocking agents, Thermo Fisher Scientific) was added, followed by gently stirring at room temperature for 2 hours for blocking. On this occasion, wells not immobilizing the VLP were also subjected to similar blocking to be used in preselection.

The solution was discarded from the wells, the wells were washed with 200 µL of a wash buffer (10 mM Hepes (pH 7.4), 150 mM NaCl, and 0.05% Tween 20) three times, and 100 µL of cDNA display (constructed from 1.5 pmol of mRNA-linker) was then put in the wells not immobilizing the VLP, followed by gently stirring at room temperature for 30 minutes to perform preselection. Subsequently, the supernatant containing cDNA display that had not bound to the blocking agent was put in the wells immobilizing the VLP, followed by gently stirring at room temperature for 30 minutes to be bound to the VLP. The supernatant was discarded, washing with 100 µL of the wash buffer was performed four times, and 100 µL of a 5% SDS solution was then added, followed by incubation at 50° C. for 15 minutes to elute the bound cDNA display.

Subsequently, the VLP-cDNA display complex obtained above was diluted to 100 µL with a dialysis selection buffer, and 10 µL of a coprecipitating agent (Quick-Precip Plus Solution, manufactured by EdgeBio) and 220 µL of 100% ethanol were added, followed by centrifugation at 20,000×g for 5 minutes. Subsequently, the supernatant was discarded, and 1 mL of 70% ethanol was added for rinsing. The tube was dried for 10 minutes, elution with 20 µL of RNase-free water was then performed, and PCR reaction was performed using GATCCCGCGAAATTAATACGACTCAC-TATAGGGGAAGTATTTTTACAACAATTACCA ACA (SEQ ID NO: 342) as a forward primer and TTTC-CACGCCGCCCCCCGTCCT (SEQ ID NO: 343) as a reverse primer. The PCR program was (a) 98° C. for 2 minutes, (b) 95° C. for 20 seconds, (c) 69° C. for 20 seconds, (d) 72° C. for 20 seconds (steps (b) to (d) were performed 25 cycles), and (e) 72° C. for 1 minute.

TABLE 9

| Composition | Content (µL) |
|---|---|
| 10× Ex Taq Buffer (manufactured by Takara Bio Inc.) | 2.5 |
| 2.5 mM dNTP mixture (manufactured by Takara Bio Inc.) | 2 |
| 20 µM forward primer (SEQ ID NO: 342) | 0.5 |
| 20 µM reverse primer (SEQ ID NO: 343) | 0.5 |
| Ethanol precipitate | 3 |
| Nuclease-free water | 16.4 |
| Ex Taq | 0.1 |

The resulting PCR product was used as library DNA in the subsequent cycle, and the operations after the transcription of library described in the above (2) were similarly performed to repeat a selection cycle.

Analysis of Genetic Sequence Information

After the in vitro selection cycle (7 cycles for GII.4 and 5 cycles for GII.3 and GII.17 based on the libraries of 7 cycles obtained by GII.4 dialysis), a sequence library was prepared by the following method, and the sequence information was analysed. The preparation of the sequence library and the sequencing were performed according to the 16S Metagenomic Sequencing Library Preparation protocol (manufactured by Illumina, Inc.).

1) Amplicon PCR

The reagents shown in Table 10 were mixed, and PCP was performed by the following program:
at 95° C. for 3 minutes;
23 cycles of the following reactions;
at 95° C. for 30 seconds, at 55° C. for 30 seconds, and at 72° C. for 30 seconds, at 72° C. for 5 minutes; and holding at 4° C.

TABLE 10

| Composition of solution | |
|---|---|
| Sequence library (5 ng/μL) | 2.5 μL |
| Amplicon PCR Forward Primer 1 μM (SEQ ID NO: 344) | 5 μL |
| Amplicon PCR Forward Primer 1 μM (SEQ ID NO: 345) | 5 μL |
| 2× KAPA HiFi Hotstart ReadyMix (manufactured by NIPPON Genetics Co., Ltd.) | 12.5 μL |
| Total | 25 μL |

SEQ ID NO: 344:
TCGTCGGCAGCGTCAGATGTGTATAAGAGACAGCATTCTACAACTACAAG

CCACCATG

SEQ ID NO: 345:
GTCTCGTGGGCTCGGAGATGTGTATAAGAGACAGTTTCCACGCCGCCCCC

CGTCCTGCTTC

2) Clean Up

The Amplicon PCR product was purified using AMPure XP beads (manufactured by Beckman Coulter, Inc.). To the plate including the PCR product, 20 μL of the AMPure XP beads were added and the mixture was gently mixed by pipetting with a micropipette 10 times, followed by leaving to stand at room temperature for 5 minutes. The plate was placed on a magnetic stand and was left to stand for 2 minutes, and the supernatant was then discarded. While the plate was being placed on the magnetic stand, 200 μL of 80% ethanol was added to each well, and after leaving to stand for 30 seconds, the supernatant was discarded. This procedure was repeated twice. The ethanol was air-dried by leaving to stand for 10 minutes, the plate was then taken out from the magnetic stand, and 52.5 μL of 10 mM Tris pH 8.5 solution was added to each well, followed by leaving to stand at room temperature for 2 minutes. The plate was placed on the magnetic stand and was left to stand for 2 minutes again, and 50 μL of the solution in each well was transferred to the corresponding well of a new 96-well PCR plate.

3) Index PCR

A PCR reaction was performed for adding an adaptor and an index sequence for sequencing to the purified Amplicon PCR product.

The reagents shown in Table 11 were mixed, and PCR was performed by the following program:

at 95° C. for 3 minutes;

8 cycles of the following reactions;

at 95° C. for 30 seconds, at 55° C. for 30 seconds, and at 72° C. for 30 seconds, at 72° C. for 5 minutes; and holding at 4° C.

TABLE 11

| Composition of solution | |
|---|---|
| Purified Amplicon PCP product | 2.5 μL |
| Nextera XT Index Primer 1 (N7xx) (SEQ ID NOs: 346 and 347) | 2.5 μL |
| Nextera XT Index Primer 2 (S5xx) (SEQ ID NOs: 348 and 349) | 2.5 μL |
| 2× KAPA HiFi Hotstart ReadyMix | 12.5 μL |
| UltraPure Water (manufactured by invitrogen) | 5 μL |
| Total | 25 μL |

The used Index Primer set is shown in the following Table 12.

TABLE 12

| Index Primer set | | |
|---|---|---|
| | Centrifugation | Dialysis |
| Run 1 (S511) | S511, N723 | S511, N729 |
| Run 2 (S510) | S510, N723 | S510, N729 |

SEQ ID NO: 346 (N723):
CAAGCAGAAGACGGCATACGAGATTAGCGCTCGTCTCGTGGGCTCGG

SEQ ID NO: 347 (N729):
CAAGCAGAAGACGGCATACGAGATTCGACGTCGTCTCGTGGGCTCGG

SEQ ID NO: 348 (S511):
AATGATACGGCGACCACCGAGATCTACACTCTCTCCGTCGTCGGCAGC

GTC

SEQ ID NO: 349 (S510):
AATGATACGGCGACCACCGAGATCTACACCGTCTAATTCGTCGGCAGC

GTC

4) Clean Up 2

The Index PCR product was purified using AMPure XP beads (manufactured by Beckman Coulter, Inc.). To the plate including the PCR product, 56 μL of the AMPure XP beads were added and the mixture was gently mixed by pipetting with a micropipette 10 times, followed by leaving to stand at room temperature for 5 minutes. The plate was placed on a magnetic stand and was left to stand for 2 minutes, and the supernatant was then discarded. While the plate was being placed on the magnetic stand, 200 μL of 80% ethanol was added to each well, and after leaving to stand for 30 seconds, the supernatant was discarded. This procedure was repeated twice. The ethanol was air-dried by leaving to stand for 10 minutes, the plate was then taken out from the magnetic stand, and 25 μL of 10 mM Tris pH 8.5 solution was added to each well, followed by leaving to stand at room temperature for 2 minutes. The plate was placed on the magnetic stand and was left to stand for 2 minutes again, and 50 μL of the solution in each well was transferred to the corresponding well of a new 96-well PCR plate.

The purified Index PCR product was validated using Bioanalyzer DNA 1000 Chip (manufactured by Agilent Technologies, Inc.).

5) qPCR

The purified Index PCR product was subjected to qPCR using Kapa Library Quantification Kit (manufactured by NIPPON Genetics Co., Ltd.).

A mixture of 12 μL of Kapa SYBR FAST qPCR Master Mix to which Primer Mix was added in advance, 4 μL of UltraPure Water, and 4 μL of a 100-fold dilution of the Index PCR product was subjected to qPCR. As the samples for a standard curve, Std 1 to 6 included in the kit were used.

The PCR was performed by the following program:
at 95° C. for 5 minutes; and
35 cycles of the following reactions;
at 95° C. for 30 seconds, and
at 60° C. for 45 seconds.

A standard curve was drawn from the Ct values of Std 1 to 6, and sample concentration was calculated.

6) Preparing DNA Libraries for Sequencing

The Reagent Cartridge of Miseq Reagent Hit V3 150 cycles (manufactured by Illumina, Inc.) was thawed in a water bath, and the HT1 buffer included in the kit was thawed at room temperature and ice-cooled.

The Index PCR product having a concentration known by qPCR was diluted to 4 nM with UltraPure Water. A mixture of 5 μL of this 4 nM dilution of the sample and 5 μL of 0.2 N NaOH (prepared by diluting 10 N NaOH aqueous solution (manufactured by FUJIFILM Wako Pure Chemical Corporation) to 0.2 N with UltraPure Water) was left to stand at room temperature for 5 minutes. Subsequently, 990 μL of ice-cooled HT1 buffer was added thereto to obtain 1 mL of a 20 pM denatured library.

A mixture of 180 of the 20 pM denatured library and 420 μL of ice-cooled HT1 buffer was prepared as 600 μL of a 6 pM library. In addition, a mixture of 30 μL of a 20 pM PhiX DNA denatured in advance and 10 μL of ice-cooled HT1 buffer was prepared as a 15 pM denatured PhiX. A mixture of 30 μL of the 15 pM denatured PhiX and 570 μL of the 6 pM denatured library in total of 600 μL was added to "Load Samples" (position 17) of the Reagent Cartridge thawed in a water bath.

7)) Starting the Run

Flow Cell washed with Milli-Q water and 99.5% ethanol was set to Miseq (manufactured by Illumina, Inc.) subjected to Maintainance Wash with 0.5% Tween 20, and a PR2 bottle and a reagent-filled cartridge were set, followed by sequencing.

8) Analysis of Gene Information

The Fastq file of the obtained sequence was converted to a Fasta file, all of the obtained sequences were simultaneously translated from the first base of the start codon (ATG) at position 115 to the third base of the cysteine codon (TGC) at position 156 of the library sequence (SEQ ID NO: 337) using software MEGA. After the translation, the amino acid 7 residues upstream from the terminal cysteine was filtered with cysteine using the filter function of Excel to obtain 4357 peptide aptamer sequences.

9) Selection of Sequence

The obtained 4357 peptide aptamer sequences were subjected to cluster analysis and appearance frequency analysis, and the peptides shown in SEQ ID NOs: 1 to 327 were selected as peptides that specifically bind to norovirus. Among these peptides, Table 18 shows 260 peptide aptamer sequences that fall within the requirements of a hamming distance of 5 or less and forming a cluster including 5 or more sequences, Table 19 shows 104 peptide aptamer sequences that fall within the requirements of a q-gram distance divided into 3-character strings of 4 or less and forming a cluster including 3 or more sequences, and Table 20 shows 31 peptide aptamer sequences having an appearance frequency of 10 or more.

Example 2: Interaction With VLPs

Synthesis of Peptide

Peptides were synthesized by Fmoc solid synthesis in a nitrogen atmosphere using an automated peptide synthesizer Liberty Blue (manufactured by CEM Corporation). The resin used was Fmoc-Lys (Mtt)-Wang resin (manufactured by Merck Millipore S.A.S.) or Fmoc-Cys (Trt)-Wang Resin (manufactured by PEPTIDE INSTITUTE, INC.). N,N-Dimethylformamide: DMF (manufactured by FUJIFILM Wako Pure Chemical Corporation) was used as a solvent, and piperidine (manufactured by FUJIFILM Wako Pure Chemical Corporation) diluted with DMF to a predetermined concentration was used as a deprotecting agent. Diisopropylcarbodiimide (manufactured by Tokyo Chemical Industry Co., Ltd.) and ethyl cyanoglyoxylate-2-oxime: Oxyma (manufactured by WATANABE CHEMICAL INDUSTRIES, LTD.) diluted with DMF to predetermined concentrations were used as a coupling reaction accelerator and an optical activity inhibitor, respectively. The synthesis reaction was performed according to the synthesis program provided in the apparatus.

Introduction of Spacer by Manual Synthesis

A synthesis reaction was performed using a manual peptide synthesizer Petisyzer (manufactured by HiPep Laboratories). The peptide synthesized using Fmoc-Lys (Mtt)-Wang resin as the resin was brought into contact with a mixture solution of a DMF solution of 20% Diboc (manufactured by Tokyo Chemical Industry Co., Ltd.) and N,N-Diisopropylethylamine (DIEA, manufactured by WATANABE CHEMICAL INDUSTRIES, LTD.) in an amount of 10 equivalents of the synthesized peptide at room temperature for 2 hours to protect the N-terminus with a Boc group. After washing with DMF and dichloromethane (DCM, manufactured by FUJIFILM Wako Pure Chemical Corporation), the Mtt group was deprotected with a mixture solution of trifluoroacetic acid (TFA, manufactured by FUJIFILM Wako Pure Chemical Corporation), triisopropylsilane (TIS, manufactured by Tokyo Chemical Industry Co., Ltd.), and DCM (TFA:TIS:DCM=2:5:93).

A mixture solution prepared at the following ratio (Table 13) was added to the peptide of which the Mtt group was deprotected, followed by stirring at room temperature for 1 hour to introduce a PEG3 sequence. After the reaction, washing with DMF was performed, and the Fmoc group added to PEG3 was deprotected with a 20% piperidine DMF solution.

TABLE 13

| Reagent name | Equivalent |
| --- | --- |
| 1-[Bis(dimethylamino)methylene]-1H-benzotriazolium 3-oxide hexafluorophosphate: HBTU (manufactured by WATANABE CHEMICAL INDUSTRIES, LTD.) | 5 |
| 1,2,3-Benzotriazol-1-ol monohydrate: HOBt (manufactured by WATANABE CHEMICAL INDUSTRIES, LTD.) | 4.5 |
| Fmoc-AEEEA-OH (manufactured by WATANABE CHEMICAL INDUSTRIES, LTD.) | 5 |
| DIEA | 10 |

Subsequently, tryptophan was introduced to the C-terminus side of the PEG3 sequence by using a mixture solution prepared at the following ratio (Table 14) and stirring at room temperature for 1 hour. After the reaction, washing with DMF was performed, and the Fmoc group added to the tryptophan was deprotected with a 20% piperidine DMF solution.

TABLE 14

| Reagent name | Equivalent |
|---|---|
| HBTU | 5 |
| HOBt | 4.5 |
| Fmoc-(Boc)-Trp (manufactured by WATANABE CHEMICAL INDUSTRIES, LTD.) | 5 |
| DIEA | 10 |

Furthermore, biotin was introduced to the C-terminus side of the tryptophan by using a mixture solution prepared at the following ratio (Table 15) and stirring at room temperature for 1 hour. After the reaction, washing with DMF was performed.

TABLE 15

| Reagent name | Equivalent |
|---|---|
| HBTU | 5 |
| HOBt | 4.5 |
| Biotin (manufactured by Tokyo Chemical Industry Co., Ltd.) | 5 |
| DIEA | 10 |

The peptide synthesized using Fmoc-Cys-Wang resin as the resin was subjected to the addition reactions of the PEG3 sequence and tryptophan with the Liberty Blue. The addition reaction of biotin was performed using the reagents shown in Table 15 by manual synthesis with Petisyzer.

Cleavage of Peptide Attached With Spacer Sequence From Resin

The resin binding to the peptide added with a spacer sequence was washed with diethyl ether (manufactured by FUJIFILM Wako Pure Chemical Corporation) and dried. This resin was brought into contact with a mixture solution of TFA:TIS:$H_2O$=95:2.5:2.5 at room temperature for 1 hour to cleave the peptide from the resin. The resin was removed from the solution by filtration, and 5 times the amount of ice-cooled diethyl ether was added to the solution, followed by inversion and stirring to generate a precipitate. The generated precipitate was centrifuged at 13,000 rpm for 3 minutes at 20° C., and the precipitate was again washed with diethyl ether and centrifuged under the same conditions. The precipitate was dried in a draft, and the resulting powder was stored at 4° C.

Evaluation of Interaction by ELISA

The peptide was dispersed in a 10% DMF aqueous solution. The concentration was calculated by an absorptiometer and was adjusted to 50 μM with a 10% DMF aqueous solution. This was added to Pierce™ Streptavidin Coated Plates, Clear, 96-Well (manufactured by Thermo Fisher Scientific) at 100 μL/well and was left to stand at room temperature for 1 hour. The supernatant was removed, and after washing with 200 μL of PBS-T (PBS containing 0.05% Tween 20) three times, 100 μL of a GII.3, GII.4, or GII.17 VLP solution diluted to 100 ng/mL with PBS-T was added, followed by leaving to stand at room temperature for 50 minutes. The supernatant was removed, and after washing with 200 μL of PBS-T three times, 100 μL of a rabbit anti-norovirus VLP polyclonal antibody (produced using a mixture of the GII.3 and GII.17 VLPs as an antigen by outsourcing to Eurofins Genomics K.K.) diluted to 1 μg/mL with a blocking agent was added, followed by leaving to stand at room temperature for 50 minutes. The supernatant was removed, and after washing with 200 μL of PBS-T three times, 100 μL of an HRP-labeled anti-rabbit IgG antibody (manufactured by Cell Signaling Technology, Inc.) diluted 1,000-fold with a blocking solution was added, followed by leaving to stand at room temperature for 50 minutes. The supernatant was removed, and after washing with 200 μL of PBS-T three times, 100 μL of 3,3',5,5'-tetramethylbenzidine (manufactured by Abcam plc.) was added, followed by leaving to stand at room temperature for 15 minutes. As a reaction stopping solution, 100 μL of 0.5 M sulfuric acid was added, and the absorbance at 450 nm was measured with a multiplate reader (manufactured by Molecular Devices, LLC.). The results are shown in FIG. 4.

Calculation of KD Value by Bio-Layer Interferometry: BLI Method

The apparatus used was BLItz™ (manufactured by ForteBio). The tip of SA chip (manufactured by ForteBio) was kept in contact with purified water for 1 minute for hydration and was then kept in contact with a 1% BSA aqueous solution for 1 hour for blocking. The SA chip subjected to blocking treatment was set to the measuring unit of the BLItz™ main body, and measurement was performed according to the program shown in Table 16. The peptides of SEQ ID NOs: 103, 167, 205, 263, 283, 288, and 302 were used, and the concentration was adjusted to 100 μM. The concentrations of each of the GII.3 and GII.17 VLPs were adjusted to 1, 0.1, 0.01, and 0.001 mg/mL. The measurement data were analyzed using the attached software, and the KD value was calculated based on the Ka and Kd values. The results are shown in Table 17.

TABLE 16

| Operation | Used solution | Time [sec] |
|---|---|---|
| Baseline | PBS | 30 |
| Peptide bonding | 100 μM Peptide | 60 |
| Wash | PBS | 30 |
| Association | VLP | 90 |
| Dissociation | PBS | 60 |

TABLE 17

| | GII.3 | | | GII.17 | | |
|---|---|---|---|---|---|---|
| | KD[M] | ka[1/Ms] | kd[1/s] | KD[M] | ka[1/Ms] | kd[1/s] |
| No.103 | 8.07E−09 | 2.10E+06 | 1.70E−02 | 8.13E−09 | 1.38E+06 | 1.12E−02 |
| No.167 | 1.39E−09 | 3.14E+06 | 4.35E−03 | 6.96E−10 | 1.59E+06 | 1.11E−03 |
| No.205 | 3.16E−08 | 1.03E+06 | 1.00E−03 | 1.09E−07 | 1.69E+05 | 1.84E−02 |
| No.263 | 5.75E−08 | 8.51E+05 | 4.90E−02 | 1.91E−08 | 1.40E+05 | 8.65E−03 |

TABLE 17-continued

|  | GII.3 | | | GII.17 | | |
| --- | --- | --- | --- | --- | --- | --- |
|  | KD[M] | ka[1/Ms] | kd[1/s] | KD[M] | ka[1/Ms] | kd[1/s] |
| No.283 | 9.09E−10 | 7.86E+06 | 7.15E−03 | 1.39E−09 | 9.94E+05 | 1.38E−04 |
| No.288 | 6.86E−09 | 2.09E+06 | 1.43E−02 | 1.20E−08 | 6.20E+05 | 7.47E−03 |
| No.302 |  |  |  | 2.84E−08 | 2.28E+06 | 6.48E−02 |

TABLE 18

| Cluster | SEQ ID NO: | Sequence |
| --- | --- | --- |
| 1 | 1 | GDINVSLSLC |
|  | 2 | GDIHVSLSLC |
|  | 3 | GIVRVCLSLT |
|  | 4 | GMVRVCLSLK |
|  | 5 | GMVRVCLSLT |
| 2 | 6 | VCVFLRSMTQ |
|  | 7 | VCVFFPSMKQ |
|  | 8 | VCVFLLSMTQ |
|  | 9 | VCVFLRSMKL |
|  | 10 | VCVFLRSMKQ |
| 3 | 11 | VTRSSVPGAH |
|  | 12 | VHLSSVAGSL |
|  | 13 | VHLSSVAGSP |
|  | 14 | VGGSSVHGSS |
|  | 15 | VTMSSVSGAH |
| 4 | 16 | VSLLMASIIS |
|  | 17 | KSLLDATDNS |
|  | 18 | TSLLDARDNS |
|  | 19 | KSLLDARENS |
|  | 20 | KSLLDASDNS |
| 5 | 21 | TLLLVVMHGQ |
|  | 22 | TLMLVVMHGL |
|  | 23 | TLMLVVMHGP |
|  | 24 | TLMLVVMHGQ |
|  | 25 | TLILVVFFNR |
| 6 | 26 | VSSRVTQHRM |
|  | 27 | VSSRVTQPRT |
|  | 28 | VSSRVTQNRM |
|  | 29 | VSSRVTQTRM |
|  | 30 | RSSYVTSIRI |
| 7 | 31 | VTLNWSNSSE |
|  | 32 | VTLHWINSSD |
|  | 33 | VTLNWINSSD |
|  | 34 | VTLKWSNSAE |
|  | 35 | VTLNWVNSSD |
| 8 | 36 | IMNAEKIKGK |
|  | 37 | MKNAEKIKGK |
|  | 38 | MKHAEKIKGT |
|  | 39 | MKHAEKITGK |
|  | 40 | MKHAEKIKGK |
| 9 | 41 | CLSLQRINVM |
|  | 42 | CLSMQRIAVM |
|  | 43 | CLSMQRINVM |
|  | 44 | CLRMQRSNVR |
|  | 45 | CLSMQRMSVM |
| 10 | 46 | IVGDSIGTSL |
|  | 47 | IFGASIGTSL |
|  | 48 | IVGASIGTSL |
|  | 49 | IVGQSIEADL |
|  | 50 | IVGQSMETDL |
| 11 | 51 | SSRQGVVRAR |
|  | 52 | SSRQCVVSAR |
|  | 53 | SSRQGVVSAR |
|  | 54 | SSRPGVVSAR |
|  | 55 | SIRQVVVSAR |
| 12 | 56 | ERKSNVGHNF |
|  | 57 | ERRSNVGHNF |
|  | 58 | DRTSNVGHNF |
|  | 59 | ERKSNVGHTF |
|  | 60 | ERQSNVGHNF |
| 13 | 61 | RDKVQEFKHH |
|  | 62 | RDKVQEFKHL |
|  | 63 | RDKVQEFTHH |
|  | 64 | RDQVQEFPHH |
|  | 65 | RYKVQEFKHH |
| 14 | 66 | SDRIGRDSSS |
|  | 67 | SARTGRDSSS |
|  | 68 | SDRTGRDSSS |
|  | 69 | SDRTGRDSSL |
|  | 70 | SHTGGRDSVI |
| 15 | 71 | SKGRQAKRNH |
|  | 72 | SKGRHAKRNH |
|  | 73 | SKGRHAKRNL |
|  | 74 | SKGRHAKRNN |
|  | 75 | SKGRHATRNH |
| 16 | 76 | SGTFGNTGSN |
|  | 77 | VGWFGYTGIV |
|  | 78 | VGWFGYTGIA |
|  | 79 | VGWFGYTGMG |
|  | 80 | VGWFGYTGMV |
| 17 | 81 | KRRGGINDIA |
|  | 82 | KRSGGINDIV |
|  | 83 | KRSGGINDIA |
|  | 84 | TRSGGINDIA |
|  | 85 | KRRGGITAIA |
| 18 | 86 | SCHGLMSTCC |
|  | 87 | SCHGLTSTCC |
|  | 88 | SCPGLMSTFC |
|  | 89 | RCPGLLSPCC |
|  | 90 | SCHGLMFTCC |
| 19 | 91 | HRHHTPNSHH |
|  | 92 | NRHHTPNSHH |
|  | 93 | HRHHTPNTHH |
|  | 94 | HRHPTPNSHH |
|  | 95 | HRHHTPNSDD |
| 20 | 96 | LVGSRRTGLD |
|  | 97 | FFCSRRTGLY |
|  | 98 | FVCSRRSGLY |
|  | 99 | LGWSRRTGLY |
|  | 100 | FFWSRRTGLY |
| 21 | 101 | SFLVPVVKVM |
|  | 102 | SFLVPVVKVL |
|  | 103 | RFLVPVVKVM |
|  | 104 | SFLPVVKVM |
|  | 105 | SFLVAVVKVV |
| 22 | 106 | KFKDAKKNLM |
|  | 107 | KFKDAKKHLI |
|  | 108 | KFKDAKKNLR |
|  | 109 | KFQAAKKNLM |
|  | 110 | KFQDAKKNLM |
|  | 111 | KFTDAKTHLM |
| 23 | 112 | GKMSIWAGGE |
|  | 113 | GKMRIWAGGE |
|  | 114 | GKLSIWAGGE |
|  | 115 | GKMRMWAGGE |
|  | 116 | GKMSMWAGGE |
|  | 117 | GRMSIWAGGP |
| 24 | 118 | VALFILTSSG |
|  | 119 | VALFLLTSSC |
|  | 120 | IVELFILTRSC |
|  | 121 | VELFLFTSSC |
|  | 122 | VGLFILTSSC |
|  | 123 | VALFLLPRRC |
| 25 | 124 | NRINDITQVE |
|  | 125 | NRINDIMQVE |
|  | 126 | TRITDVTQVE |
|  | 127 | NRITAITPVE |
|  | 128 | NRINDISQVG |
|  | 129 | DRINDIAQVE |
|  | 130 | NSITDITQVE |

TABLE 18-continued

| Cluster | SEQ ID NO: | Sequence |
|---|---|---|
| 26 | 131 | IRVVDSVCGS |
|  | 132 | IRVVDSVGGS |
|  | 133 | IRVVDSVGGL |
|  | 134 | IRVVYSVHMA |
|  | 135 | IRVVYSVHMG |
|  | 136 | IRVVYSVPMA |
|  | 137 | IRFVGSVCRR |
|  | 138 | IRVVYSVHMD |
| 27 | 139 | VLWHLVFSDR |
|  | 140 | VLWHLVCRDR |
|  | 141 | VLWNVVYSDR |
|  | 142 | VLWNLVFSDR |
|  | 143 | VLWHLVWSER |
|  | 144 | VLWHLVVSER |
|  | 145 | VLWHLVVSDR |
|  | 146 | VMWHLVFSDR |
| 28 | 147 | VPVMGYIHVG |
|  | 148 | VPFMGYIHVG |
|  | 149 | VHVMGYIHVG |
|  | 150 | VTVMGYIHVG |
|  | 151 | VPVRGSIRVG |
|  | 152 | VPVMGYILVG |
|  | 153 | GPVMGYSHVG |
|  | 154 | VPVRGYVFVG |
| 29 | 155 | DFTARDCVAF |
|  | 156 | DFTARDCVAC |
|  | 157 | DFTARECVAF |
|  | 158 | DFAVWDCVAF |
|  | 159 | DINARNCVAF |
|  | 160 | DFTARVCVAF |
|  | 161 | DFTGRDCVAF |
|  | 162 | DFTARDYVAF |
|  | 163 | DFTAWDCVAF |
| 30 | 164 | CVWRRRNGLY |
|  | 165 | FVWRRRHCLY |
|  | 166 | FVWRRRTGLS |
|  | 167 | FVWRRRAGLY |
|  | 168 | FGWRRRAGLY |
|  | 169 | FVWRRRPGLS |
|  | 170 | CVWRRRTGLS |
|  | 171 | FVWRRSGLF |
|  | 172 | SVWRRRTGLY |
| 31 | 173 | SSIVSLAGDL |
|  | 174 | SSIVSLAGEV |
|  | 175 | SSIVSRAGDL |
|  | 176 | SSIVSLSGDL |
|  | 177 | SSIVSLAGNL |
|  | 178 | SSIVSLAGDR |
|  | 179 | SSIVCLAGDL |
|  | 180 | SSIVSLAGYL |
|  | 181 | SSIGSLAGDL |
|  | 182 | SSIVSRAGDL |
|  | 183 | SSIVSIAGDL |
|  | 184 | SSVVSLAGDF |
|  | 185 | SSIVSLAGEL |
|  | 186 | SSLVSLACAL |
|  | 187 | SSIVSLADDL |
|  | 188 | SSIVSLAGDV |
|  | 189 | SRIVSLAGDL |
|  | 190 | SSIVSVAGDL |
|  | 191 | SCIVSLAGDL |
|  | 192 | SSVVCLAGEL |
|  | 193 | SSIVSFAGDF |
|  | 194 | SSVVSLAGDL |
|  | 195 | SSMVSLAGDL |
|  | 196 | SRSVSLAGDR |
|  | 197 | SSMVSFAGDL |
|  | 198 | RSIVSLAGDL |
|  | 199 | SSIVSLVGDL |
|  | 200 | SSIVSLEGDL |
|  | 201 | SSIVSLAGGL |
|  | 202 | SSIVSLLGDL |
|  | 203 | SSIVSLAGAL |
|  | 204 | GSIVSLAGDL |
| 32 | 205 | FVWSRRTGLY |
|  | 206 | FVWSRQTGLY |
|  | 207 | FVWSRRTGIY |
|  | 208 | FVWSLLTVLY |
|  | 209 | FVWSRRAGLY |
|  | 210 | FVWSRRIGVY |
|  | 211 | FVWNRRTGLY |
|  | 212 | FVWSRRNGLY |
|  | 213 | FVWRRRTGLY |
|  | 214 | LVWSRRTGLY |
|  | 215 | FVLSRRTCIY |
|  | 216 | FVWSKRTGLY |
|  | 217 | FVWSRRPGLY |
|  | 218 | FVWSRRSGLY |
|  | 219 | FVWSRWTGLY |
|  | 220 | FVWSRQTSLY |
|  | 221 | FVWSRRTGLD |
|  | 222 | FVWSRRTGRY |
|  | 223 | VVWSRRTGLY |
|  | 224 | FVGSRRTGLY |
|  | 225 | FVWSRRTSLY |
|  | 226 | FFWSMRTGLY |
|  | 227 | FVWSRRTGLF |
|  | 228 | FVWSGRIGVY |
|  | 229 | FVWSRRTGIF |
|  | 230 | FVWSRRTGLS |
|  | 231 | FVWSRRTVIL |
|  | 232 | FVWSRRTVLL |
|  | 233 | VVWSRRTGRY |
|  | 234 | FVWCRRTGLY |
|  | 235 | FVWSRRTGFY |
|  | 236 | FVWCRWTGLY |
|  | 237 | FVWSRRTDLY |
|  | 238 | FVWSRRTVLY |
|  | 239 | FVWSWRTGLY |
|  | 240 | FVWCRRTGIY |
|  | 241 | FVWSMRTGLY |
|  | 242 | FVWSRRTGVC |
|  | 243 | FVWSWRIGLY |
|  | 244 | FVWSRQTGVY |
|  | 245 | FVWSRRIGLY |
|  | 246 | FVWSRRTCLY |
|  | 247 | FVWSRRTGSY |
|  | 248 | FVWSRRSGIY |
|  | 249 | FVWSRRTGVY |
|  | 250 | FFWSRRTCIY |
|  | 251 | FVLSRRTGLY |
|  | 252 | FVWSGRTGLY |
|  | 253 | FVWSWRSGLY |
|  | 254 | FVWSRRTVLF |
|  | 255 | FVWSRWAGLY |
|  | 256 | FGWSMRTGLY |
|  | 257 | FVWGRRTGLY |
|  | 258 | FVWSRRTGLC |
|  | 259 | FVWRRRTSLY |
|  | 260 | FVWSRWTGLC |

TABLE 19

| Cluster | SEQ ID NO: | Sequence |
|---|---|---|
| 1 | 261 | ENYRWSRSIK |
|  | 262 | DNYRWSRSIK |
|  | 263 | ANYRWSRSIK |
| 2 | 6 | VCVFLRSMTQ |
|  | 9 | VCVFLRSMKL |
|  | 10 | VCVFLRSMKQ |
| 3 | 22 | TLMLVVMHGL |
|  | 23 | TLMLVVMHGP |
|  | 24 | TLMLVVMHGQ |
| 4 | 264 | TAQRLQWENR |
|  | 265 | TEQRLQWENR |
|  | 266 | TYQRLQWENR |
| 5 | 267 | IGCIVSGSNN |
|  | 268 | IGCIVSGSNT |
|  | 269 | IGCIVSGSTN |
| 6 | 270 | TFSMNTHRGA |
|  | 271 | TFSMNTHRGV |
|  | 272 | NFSMNTHRGA |

TABLE 19-continued

| Cluster | SEQ ID NO: | Sequence |
|---|---|---|
| 7 | 273 | SNTRGNMDDS |
|  | 274 | SNTRGNMDDY |
|  | 275 | SNTRGNMDDF |
| 8 | 276 | QTGHLNSRHY |
|  | 277 | QTGHLNSRHD |
|  | 278 | PTGHLNSRHD |
| 9 | 72 | SKGRHAKRNH |
|  | 73 | SKGRHAKRNL |
|  | 74 | SKGRHAKRNN |
| 10 | 279 | ITQMNRVVEK |
|  | 280 | ISQMNRVVEK |
|  | 281 | INQMNRVVEK |
| 11 | 282 | RSMSLHVSMI |
|  | 283 | RSMSLHVSMT |
|  | 284 | RSMSLHVSMR |
| 12 | 285 | QVLGQNEHED |
|  | 286 | QVLGQNEHEF |
|  | 287 | QVLGQNEHEY |
| 13 | 82 | KRSGGINDIV |
|  | 83 | KRSGGINDIA |
|  | 84 | TRSGGINDIA |
| 14 | 134 | IRVVYSVHMA |
|  | 135 | IRVVYSVHMG |
|  | 138 | IRVVYSVHMD |
| 15 | 77 | VGWFGYTGIV |
|  | 78 | VGWFGYTGIA |
|  | 79 | VGWFGYTGMG |
|  | 80 | VGWFGYTGMV |
| 16 | 288 | CKARSARGVS |
|  | 289 | CTARSARGVS |
|  | 290 | GKARSARGVS |
| 17 | 291 | IVMTPNAKDH |
|  | 292 | IVMTPNAKYH |
|  | 293 | IVMTPNAKYP |
| 18 | 294 | ANIDENHYGA |
|  | 295 | ENIDFNHYGA |
|  | 296 | ENIDFNHYGV |
| 19 | 297 | KAKLTEHSHH |
|  | 298 | KAKLTEHSPH |
|  | 299 | KAKLTEHSHP |
| 20 | 205 | FVWSRRTGLY |
|  | 214 | LVWSRRTGLY |
|  | 221 | FVWSRRTGLD |
|  | 223 | VVWSRRTGLY |
|  | 227 | FVWSRRTGLF |
|  | 230 | FVWSRRTGLS |
|  | 258 | FVWSRRTGLC |
| 21 | 173 | SSIVSLAGDL |
|  | 174 | SSIVSLAGEV |
|  | 177 | SSIVSLAGNL |
|  | 178 | SSIVSLAGDR |
|  | 180 | SSIVSLAGYL |
|  | 185 | SSIVSLAGEL |
|  | 188 | SSIVSLAGDV |
|  | 201 | SSIVSLAGGL |
|  | 203 | SSIVSLAGAL |
| 22 | 147 | VPVMGYIHVG |
|  | 149 | VHVMGYIHVG |
|  | 150 | VTVMGYIHVG |
| 23 | 207 | FVWSRRTGIY |
|  | 229 | FVWSRRTGIF |
|  | 235 | FVWSRRTGFY |
|  | 242 | FVWSRRTGVC |

TABLE 19-continued

| Cluster | SEQ ID NO: | Sequence |
|---|---|---|
|  | 247 | FVWSRRTGSY |
|  | 249 | FVWSRRTGVY |
| 24 | 213 | FVWRRRTGLY |
|  | 166 | FVWRRRTGLS |
|  | 170 | CVWRRRTGLS |
|  | 172 | SVWRRRTGLY |
| 25 | 101 | SFLVPVVKVM |
|  | 102 | SFLVPVVKVL |
|  | 103 | RFLVPVVKVM |
| 26 | 226 | FFWSMRTGLY |
|  | 241 | FVWSMRTGLY |
|  | 256 | FGWSMRTGLY |
| 27 | 231 | FVWSRRTVIL |
|  | 232 | FVWSRRTVLL |
|  | 238 | FVWSRRTVLY |
|  | 254 | FVWSRRTVLF |
| 28 | 234 | FVWCRRTGLY |
|  | 240 | FVWCRRTGIY |
|  | 300 | FVWCRRTGLC |
| 29 | 189 | SRIVSLAGDL |
|  | 191 | SCIVSLAGDL |
|  | 198 | RSIVSLAGDL |
|  | 204 | GSIVSLAGDL |

TABLE 20

| SEQ ID NO: | Sequence | Appearance Frequency | SEQ ID NO: | Sequence | Appearance Frequency |
|---|---|---|---|---|---|
| 301 | KSLLDARDNS | 21 | 315 | VAIDISIRMR | 11 |
| 302 | VWWGRRISRF | 20 | 316 | VSFSCHACST | 11 |
| 303 | ISNVRGSYVD | 18 | 317 | YLSCDYVFCG | 11 |
| 132 | IRVVDSVGGS | 16 | 318 | TDTLHSIKLV | 11 |
| 304 | RRGVCSGPGV | 15 | 319 | STGPVVNTQY | 11 |
| 305 | IKRDFCGCYR | 15 | 320 | SLTSMTHSTK | 11 |
| 267 | IGCIVSGSNN | 15 | 321 | TLSNDTGDLT | 11 |
| 306 | VLTSVPELRG | 14 | 322 | SRGFSMKRPA | 11 |
| 307 | MIDSRIPREF | 14 | 323 | GVGCIMSSIG | 11 |
| 308 | LILRVFGRWG | 13 | 28 | VSSRVTQNRM | 10 |
| 309 | VFFVSSRNRA | 12 | 324 | SMSCVDSTSV | 10 |
| 310 | VISFGGRRFG | 12 | 325 | RSNTKIMMVN | 10 |
| 311 | SVSTMSAFCL | 12 | 326 | IQRTRTDQAN | 10 |
| 312 | KNLKKHTGNT | 12 | 112 | GKMSIWAGGE | 10 |
| 313 | GVGLNSVDRD | 12 | 327 | GEFSCVIASV | 10 |
| 314 | DPRISTGNVF | 12 |  |  |  |

What is claimed is:

1. A norovirus-binding peptide consisting of an amino acid sequence selected from the group consisting of SEQ ID NOs: 1-71 and 73.

2. The norovirus-binding peptide according to claim 1, wherein the amino acid sequence selected from the group consisting of SEQ ID NOs: 1-71 and 73 is an amino acid sequence selected from the group consisting of SEQ ID NOs: 103, 167, 205, 263, 283, 288 and 302.

3. A norovirus-binding peptide consisting of the amino acid sequence selected from the group consisting of SEQ ID NOs: 1-71 and 73-327 according to claim 1 with a cysteine residue added to either or both of an N-terminus and a C-terminus thereof.

4. The norovirus-binding peptide according to claim 3, wherein the cysteine residue is added to the N-terminus and the C-terminus of the amino acid sequence selected from the group consisting of SEQ ID NOs: 1-71 and 73-327.

5. The norovirus-binding peptide according to claim 4, wherein the cysteine residue added to the N-terminus and the cysteine residue added to the C-terminus of the peptide consisting of an amino acid sequence selected from the group consisting of SEQ ID NOs: 1-71 and 73-327 are linked to each other via a disulfide bond to form a ring.

6. A norovirus-binding peptide consisting of an amino acid sequence of the peptide according to claim 1 with 1 to 20 amino acids added to either or both of the N-terminus and the C-terminus of the peptide.

7. A method for detecting norovirus, the method comprising
    (a) bringing a norovirus-binding peptide into contact with a sample that contains or may contain norovirus, and
    (b) detecting whether the norovirus-binding peptide that was in contact with the sample bound to norovirus that were in the sample;
    wherein the amino acid sequence of norovirus-binding peptide consists of an amino acid sequence selected from the group consisting of SEQ ID NOs: 1-71 and 73-327.

8. A norovirus detection kit comprising the norovirus-binding peptide according to claim 1.

* * * * *

UNITED STATES PATENT AND TRADEMARK OFFICE
CERTIFICATE OF CORRECTION

PATENT NO. : 12,378,287 B2
APPLICATION NO. : 17/613331
DATED : August 5, 2025
INVENTOR(S) : Yoshitaka Ito et al.

It is certified that error appears in the above-identified patent and that said Letters Patent is hereby corrected as shown below:

In the Claims

At Column 145, Claim 1, Lines 2-4 please delete "an amino acid sequence selected from the group consisting of SEQ ID NOs: 1-71 and 73" and replace with "an amino acid sequence selected from the group consisting of SEQ ID NOs: 1-71 and 73-327."

At Column 145, Claim 2, Lines 6-7 please delete "wherein the amino acid sequence selected from the group consisting of SEQ ID NOs: 1-71 and 73" and replace with "wherein the amino acid sequence selected from the group consisting of SEQ ID NOs: 1-71 and 73-327."

Signed and Sealed this
Ninth Day of September, 2025

Coke Morgan Stewart
*Acting Director of the United States Patent and Trademark Office*

SEQUENCE LISTING

```
<160> NUMBER OF SEQ ID NOS: 350

<210> SEQ ID NO 1
<211> LENGTH: 10
<212> TYPE: PRT
<213> ORGANISM: Artificial Sequence
<220> FEATURE:
```

<223> OTHER INFORMATION: Designed peptide

<400> SEQUENCE: 1

Gly Asp Ile Asn Val Ser Leu Ser Leu Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Designed peptide

<400> SEQUENCE: 2

Gly Asp Ile His Val Ser Leu Ser Leu Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Designed peptide

<400> SEQUENCE: 3

Gly Ile Val Arg Val Cys Leu Ser Leu Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Designed peptide

<400> SEQUENCE: 4

Gly Met Val Arg Val Cys Leu Ser Leu Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Designed peptide

<400> SEQUENCE: 5

Gly Met Val Arg Val Cys Leu Ser Leu Thr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Designed peptide

<400> SEQUENCE: 6

Val Cys Val Phe Leu Arg Ser Met Thr Gln
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Designed peptide

<400> SEQUENCE: 7

Val Cys Val Phe Phe Pro Ser Met Lys Gln
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Designed peptide

<400> SEQUENCE: 8

Val Cys Val Phe Leu Leu Ser Met Thr Gln
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Designed peptide

<400> SEQUENCE: 9

Val Cys Val Phe Leu Arg Ser Met Lys Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Designed peptide

<400> SEQUENCE: 10

Val Cys Val Phe Leu Arg Ser Met Lys Gln
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Designed peptide

<400> SEQUENCE: 11

Val Thr Arg Ser Ser Val Pro Gly Ala His
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Designed peptide

<400> SEQUENCE: 12

Val His Leu Ser Ser Val Ala Gly Ser Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Designed peptide

```
<400> SEQUENCE: 13

Val His Leu Ser Ser Val Ala Gly Ser Pro
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Designed peptide

<400> SEQUENCE: 14

Val Gly Gly Ser Ser Val His Gly Ser Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Designed peptide

<400> SEQUENCE: 15

Val Thr Met Ser Ser Val Ser Gly Ala His
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Designed peptide

<400> SEQUENCE: 16

Val Ser Leu Leu Met Ala Ser Ile Ile Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Designed peptide

<400> SEQUENCE: 17

Lys Ser Leu Leu Asp Ala Thr Asp Asn Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Designed peptide

<400> SEQUENCE: 18

Thr Ser Leu Leu Asp Ala Arg Asp Asn Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Designed peptide

<400> SEQUENCE: 19
```

```
Lys Ser Leu Leu Asp Ala Arg Glu Asn Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Designed peptide

<400> SEQUENCE: 20

Lys Ser Leu Leu Asp Ala Ser Asp Asn Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Designed peptide

<400> SEQUENCE: 21

Thr Leu Leu Leu Val Val Met His Gly Gln
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Designed peptide

<400> SEQUENCE: 22

Thr Leu Met Leu Val Val Met His Gly Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Designed peptide

<400> SEQUENCE: 23

Thr Leu Met Leu Val Val Met His Gly Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Designed peptide

<400> SEQUENCE: 24

Thr Leu Met Leu Val Val Met His Gly Gln
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Designed peptide

<400> SEQUENCE: 25
```

Thr Leu Ile Leu Val Val Phe Phe Asn Arg
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Designed peptide

<400> SEQUENCE: 26

Val Ser Ser Arg Val Thr Gln His Arg Met
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Designed peptide

<400> SEQUENCE: 27

Val Ser Ser Arg Val Thr Gln Pro Arg Thr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Designed peptide

<400> SEQUENCE: 28

Val Ser Ser Arg Val Thr Gln Asn Arg Met
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Designed peptide

<400> SEQUENCE: 29

Val Ser Ser Arg Val Thr Gln Thr Arg Met
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Designed peptide

<400> SEQUENCE: 30

Arg Ser Ser Tyr Val Thr Ser Ile Arg Ile
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Designed peptide

<400> SEQUENCE: 31

Val Thr Leu Asn Trp Ser Asn Ser Ser Glu

```
<210> SEQ ID NO 32
<211> LENGTH: 10
<212> TYPE: PRT
<213> ORGANISM: Artificial Sequence
<220> FEATURE:
<223> OTHER INFORMATION: Designed peptide

<400> SEQUENCE: 32

Val Thr Leu His Trp Ile Asn Ser Ser Asp
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Designed peptide

<400> SEQUENCE: 33

Val Thr Leu Asn Trp Ile Asn Ser Ser Asp
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Designed peptide

<400> SEQUENCE: 34

Val Thr Leu Lys Trp Ser Asn Ser Ala Glu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Designed peptide

<400> SEQUENCE: 35

Val Thr Leu Asn Trp Val Asn Ser Ser Asp
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Designed peptide

<400> SEQUENCE: 36

Ile Met Asn Ala Glu Lys Ile Lys Gly Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Designed peptide

<400> SEQUENCE: 37

Met Lys Asn Ala Glu Lys Ile Lys Gly Lys
1               5                   10
```

```
<210> SEQ ID NO 38
<211> LENGTH: 10
<212> TYPE: PRT
<213> ORGANISM: Artificial Sequence
<220> FEATURE:
<223> OTHER INFORMATION: Designed peptide

<400> SEQUENCE: 38

Met Lys His Ala Glu Lys Ile Lys Gly Thr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Designed peptide

<400> SEQUENCE: 39

Met Lys His Ala Glu Lys Ile Thr Gly Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Designed peptide

<400> SEQUENCE: 40

Met Lys His Ala Glu Lys Ile Lys Gly Lys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Designed peptide

<400> SEQUENCE: 41

Cys Leu Ser Leu Gln Arg Ile Asn Val Met
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Designed peptide

<400> SEQUENCE: 42

Cys Leu Ser Met Gln Arg Ile Ala Val Met
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Designed peptide

<400> SEQUENCE: 43

Cys Leu Ser Met Gln Arg Ile Asn Val Met
1               5                   10
```

```
<210> SEQ ID NO 44
<211> LENGTH: 10
<212> TYPE: PRT
<213> ORGANISM: Artificial Sequence
<220> FEATURE:
<223> OTHER INFORMATION: Designed peptide

<400> SEQUENCE: 44

Cys Leu Arg Met Gln Arg Ser Asn Val Arg
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Designed peptide

<400> SEQUENCE: 45

Cys Leu Ser Met Gln Arg Met Ser Val Met
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Designed peptide

<400> SEQUENCE: 46

Ile Val Gly Asp Ser Ile Gly Thr Ser Leu
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Designed peptide

<400> SEQUENCE: 47

Ile Phe Gly Ala Ser Ile Gly Thr Ser Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Designed peptide

<400> SEQUENCE: 48

Ile Val Gly Ala Ser Ile Gly Thr Ser Leu
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Designed peptide

<400> SEQUENCE: 49

Ile Val Gly Gln Ser Ile Glu Ala Asp Leu
1               5                   10
```

```
<210> SEQ ID NO 50
<211> LENGTH: 10
<212> TYPE: PRT
<213> ORGANISM: Artificial Sequence
<220> FEATURE:
<223> OTHER INFORMATION: Designed peptide

<400> SEQUENCE: 50

Ile Val Gly Gln Ser Met Glu Thr Asp Leu
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Designed peptide

<400> SEQUENCE: 51

Ser Ser Arg Gln Gly Val Val Arg Ala Arg
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Designed peptide

<400> SEQUENCE: 52

Ser Ser Arg Gln Cys Val Val Ser Ala Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Designed peptide

<400> SEQUENCE: 53

Ser Ser Arg Gln Gly Val Val Ser Ala Arg
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Designed peptide

<400> SEQUENCE: 54

Ser Ser Arg Pro Gly Val Val Ser Ala Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Designed peptide

<400> SEQUENCE: 55

Ser Ile Arg Gln Val Val Val Ser Ala Arg
1               5                   10

<210> SEQ ID NO 56
```

```
<211> LENGTH: 10
<212> TYPE: PRT
<213> ORGANISM: Artificial Sequence
<220> FEATURE:
<223> OTHER INFORMATION: Designed peptide

<400> SEQUENCE: 56

Glu Arg Lys Ser Asn Val Gly His Asn Phe
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Designed peptide

<400> SEQUENCE: 57

Glu Arg Arg Ser Asn Val Gly His Asn Phe
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Designed peptide

<400> SEQUENCE: 58

Asp Arg Thr Ser Asn Val Gly His Asn Phe
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Designed peptide

<400> SEQUENCE: 59

Glu Arg Lys Ser Asn Val Gly His Thr Phe
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Designed peptide

<400> SEQUENCE: 60

Glu Arg Gln Ser Asn Val Gly His Asn Phe
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Designed peptide

<400> SEQUENCE: 61

Arg Asp Lys Val Gln Glu Phe Lys His His
1               5                   10

<210> SEQ ID NO 62
<211> LENGTH: 10
```

```
<212> TYPE: PRT
<213> ORGANISM: Artificial Sequence
<220> FEATURE:
<223> OTHER INFORMATION: Designed peptide

<400> SEQUENCE: 62

Arg Asp Lys Val Gln Glu Phe Lys His Leu
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Designed peptide

<400> SEQUENCE: 63

Arg Asp Lys Val Gln Glu Phe Thr His His
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Designed peptide

<400> SEQUENCE: 64

Arg Asp Gln Val Gln Glu Phe Pro His His
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Designed peptide

<400> SEQUENCE: 65

Arg Tyr Lys Val Gln Glu Phe Lys His His
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Designed peptide

<400> SEQUENCE: 66

Ser Asp Arg Ile Gly Arg Asp Ser Ser Ser
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Designed peptide

<400> SEQUENCE: 67

Ser Ala Arg Thr Gly Arg Asp Ser Ser Ser
1               5                   10

<210> SEQ ID NO 68
<211> LENGTH: 10
<212> TYPE: PRT
```

```
<213> ORGANISM: Artificial Sequence
<220> FEATURE:
<223> OTHER INFORMATION: Designed peptide

<400> SEQUENCE: 68

Ser Asp Arg Thr Gly Arg Asp Ser Ser Ser
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Designed peptide

<400> SEQUENCE: 69

Ser Asp Arg Thr Gly Arg Asp Ser Ser Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Designed peptide

<400> SEQUENCE: 70

Ser His Thr Gly Gly Arg Asp Ser Val Ile
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Designed peptide

<400> SEQUENCE: 71

Ser Lys Gly Arg Gln Ala Lys Arg Asn His
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Designed peptide

<400> SEQUENCE: 72

Ser Lys Gly Arg His Ala Lys Arg Asn His
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Designed peptide

<400> SEQUENCE: 73

Ser Lys Gly Arg His Ala Lys Arg Asn Leu
1               5                   10

<210> SEQ ID NO 74
<211> LENGTH: 10
<212> TYPE: PRT
<213> ORGANISM: Artificial Sequence
```

```
<220> FEATURE:
<223> OTHER INFORMATION: Designed peptide

<400> SEQUENCE: 74

Ser Lys Gly Arg His Ala Lys Arg Asn Asn
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Designed peptide

<400> SEQUENCE: 75

Ser Lys Gly Arg His Ala Thr Arg Asn His
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Designed peptide

<400> SEQUENCE: 76

Ser Gly Thr Phe Gly Asn Thr Gly Ser Asn
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Designed peptide

<400> SEQUENCE: 77

Val Gly Trp Phe Gly Tyr Thr Gly Ile Val
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Designed peptide

<400> SEQUENCE: 78

Val Gly Trp Phe Gly Tyr Thr Gly Ile Ala
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Designed peptide

<400> SEQUENCE: 79

Val Gly Trp Phe Gly Tyr Thr Gly Met Gly
1               5                   10

<210> SEQ ID NO 80
<211> LENGTH: 10
<212> TYPE: PRT
<213> ORGANISM: Artificial Sequence
<220> FEATURE:
```

```
<223> OTHER INFORMATION: Designed peptide

<400> SEQUENCE: 80

Val Gly Trp Phe Gly Tyr Thr Gly Met Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Designed peptide

<400> SEQUENCE: 81

Lys Arg Arg Gly Gly Ile Asn Asp Ile Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Designed peptide

<400> SEQUENCE: 82

Lys Arg Ser Gly Gly Ile Asn Asp Ile Val
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Designed peptide

<400> SEQUENCE: 83

Lys Arg Ser Gly Gly Ile Asn Asp Ile Ala
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Designed peptide

<400> SEQUENCE: 84

Thr Arg Ser Gly Gly Ile Asn Asp Ile Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Designed peptide

<400> SEQUENCE: 85

Lys Arg Arg Gly Gly Ile Thr Ala Ile Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Designed peptide
```

<400> SEQUENCE: 86

Ser Cys His Gly Leu Met Ser Thr Cys Cys
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Designed peptide

<400> SEQUENCE: 87

Ser Cys His Gly Leu Thr Ser Thr Cys Cys
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Designed peptide

<400> SEQUENCE: 88

Ser Cys Pro Gly Leu Met Ser Thr Phe Cys
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Designed peptide

<400> SEQUENCE: 89

Arg Cys Pro Gly Leu Leu Ser Pro Cys Cys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Designed peptide

<400> SEQUENCE: 90

Ser Cys His Gly Leu Met Phe Thr Cys Cys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Designed peptide

<400> SEQUENCE: 91

His Arg His His Thr Pro Asn Ser His His
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Designed peptide

```
<400> SEQUENCE: 92

Asn Arg His His Thr Pro Asn Ser His His
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Designed peptide

<400> SEQUENCE: 93

His Arg His His Thr Pro Asn Thr His His
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Designed peptide

<400> SEQUENCE: 94

His Arg His Pro Thr Pro Asn Ser His His
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Designed peptide

<400> SEQUENCE: 95

His Arg His His Thr Pro Asn Ser Asp Asp
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Designed peptide

<400> SEQUENCE: 96

Leu Val Gly Ser Arg Arg Thr Gly Leu Asp
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Designed peptide

<400> SEQUENCE: 97

Phe Phe Cys Ser Arg Arg Thr Gly Leu Tyr
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Designed peptide

<400> SEQUENCE: 98
```

```
Phe Val Cys Ser Arg Arg Ser Gly Leu Tyr
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Designed peptide

<400> SEQUENCE: 99

Leu Gly Trp Ser Arg Arg Thr Gly Leu Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Designed peptide

<400> SEQUENCE: 100

Phe Phe Trp Ser Arg Arg Thr Gly Leu Tyr
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Designed peptide

<400> SEQUENCE: 101

Ser Phe Leu Val Pro Val Val Lys Val Met
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Designed peptide

<400> SEQUENCE: 102

Ser Phe Leu Val Pro Val Val Lys Val Leu
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Designed peptide

<400> SEQUENCE: 103

Arg Phe Leu Val Pro Val Val Lys Val Met
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Designed peptide

<400> SEQUENCE: 104
```

```
Ser Phe Leu Phe Pro Val Val Lys Val Met
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Designed peptide

<400> SEQUENCE: 105

Ser Phe Leu Val Ala Val Val Lys Val Val
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Designed peptide

<400> SEQUENCE: 106

Lys Phe Lys Asp Ala Lys Lys Asn Leu Met
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Designed peptide

<400> SEQUENCE: 107

Lys Phe Lys Asp Ala Lys Lys His Leu Ile
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Designed peptide

<400> SEQUENCE: 108

Lys Phe Lys Asp Ala Lys Lys Asn Leu Arg
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Designed peptide

<400> SEQUENCE: 109

Lys Phe Gln Ala Ala Lys Lys Asn Leu Met
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Designed peptide

<400> SEQUENCE: 110

Lys Phe Gln Asp Ala Lys Lys Asn Leu Met
```

```
1               5                   10
```

<210> SEQ ID NO 111
<211> LENGTH: 10
<212> TYPE: PRT
<213> ORGANISM: Artificial Sequence
<220> FEATURE:
<223> OTHER INFORMATION: Designed peptide

<400> SEQUENCE: 111

```
Lys Phe Thr Asp Ala Lys Thr His Leu Met
1               5                   10
```

<210> SEQ ID NO 112
<211> LENGTH: 10
<212> TYPE: PRT
<213> ORGANISM: Artificial Sequence
<220> FEATURE:
<223> OTHER INFORMATION: Designed peptide

<400> SEQUENCE: 112

```
Gly Lys Met Ser Ile Trp Ala Gly Gly Glu
1               5                   10
```

<210> SEQ ID NO 113
<211> LENGTH: 10
<212> TYPE: PRT
<213> ORGANISM: Artificial Sequence
<220> FEATURE:
<223> OTHER INFORMATION: Designed peptide

<400> SEQUENCE: 113

```
Gly Lys Met Arg Ile Trp Ala Gly Gly Glu
1               5                   10
```

<210> SEQ ID NO 114
<211> LENGTH: 10
<212> TYPE: PRT
<213> ORGANISM: Artificial Sequence
<220> FEATURE:
<223> OTHER INFORMATION: Designed peptide

<400> SEQUENCE: 114

```
Gly Lys Leu Ser Ile Trp Ala Gly Gly Glu
1               5                   10
```

<210> SEQ ID NO 115
<211> LENGTH: 10
<212> TYPE: PRT
<213> ORGANISM: Artificial Sequence
<220> FEATURE:
<223> OTHER INFORMATION: Designed peptide

<400> SEQUENCE: 115

```
Gly Lys Met Arg Met Trp Ala Gly Gly Glu
1               5                   10
```

<210> SEQ ID NO 116
<211> LENGTH: 10
<212> TYPE: PRT
<213> ORGANISM: Artificial Sequence
<220> FEATURE:
<223> OTHER INFORMATION: Designed peptide

<400> SEQUENCE: 116

```
Gly Lys Met Ser Met Trp Ala Gly Gly Glu
1               5                   10
```

```
<210> SEQ ID NO 117
<211> LENGTH: 10
<212> TYPE: PRT
<213> ORGANISM: Artificial Sequence
<220> FEATURE:
<223> OTHER INFORMATION: Designed peptide

<400> SEQUENCE: 117

Gly Arg Met Ser Ile Trp Ala Gly Gly Pro
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Designed peptide

<400> SEQUENCE: 118

Val Ala Leu Phe Ile Leu Thr Ser Ser Gly
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Designed peptide

<400> SEQUENCE: 119

Val Ala Leu Phe Leu Leu Thr Ser Ser Cys
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Designed peptide

<400> SEQUENCE: 120

Val Glu Leu Phe Ile Leu Thr Arg Ser Cys
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Designed peptide

<400> SEQUENCE: 121

Val Glu Leu Phe Leu Phe Thr Ser Ser Cys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Designed peptide

<400> SEQUENCE: 122

Val Gly Leu Phe Ile Leu Thr Ser Ser Cys
1               5                   10
```

<210> SEQ ID NO 123
<211> LENGTH: 10
<212> TYPE: PRT
<213> ORGANISM: Artificial Sequence
<220> FEATURE:
<223> OTHER INFORMATION: Designed peptide

<400> SEQUENCE: 123

Val Ala Leu Phe Leu Leu Pro Arg Arg Cys
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Designed peptide

<400> SEQUENCE: 124

Asn Arg Ile Asn Asp Ile Thr Gln Val Glu
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Designed peptide

<400> SEQUENCE: 125

Asn Arg Ile Asn Asp Ile Met Gln Val Glu
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Designed peptide

<400> SEQUENCE: 126

Thr Arg Ile Thr Asp Val Thr Gln Val Glu
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Designed peptide

<400> SEQUENCE: 127

Asn Arg Ile Thr Ala Ile Thr Pro Val Glu
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Designed peptide

<400> SEQUENCE: 128

Asn Arg Ile Asn Asp Ile Ser Gln Val Gly
1               5                   10

```
<210> SEQ ID NO 129
<211> LENGTH: 10
<212> TYPE: PRT
<213> ORGANISM: Artificial Sequence
<220> FEATURE:
<223> OTHER INFORMATION: Designed peptide

<400> SEQUENCE: 129

Asp Arg Ile Asn Asp Ile Ala Gln Val Glu
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Designed peptide

<400> SEQUENCE: 130

Asn Ser Ile Thr Asp Ile Thr Gln Val Glu
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Designed peptide

<400> SEQUENCE: 131

Ile Arg Val Val Asp Ser Val Cys Gly Ser
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Designed peptide

<400> SEQUENCE: 132

Ile Arg Val Val Asp Ser Val Gly Gly Ser
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Designed peptide

<400> SEQUENCE: 133

Ile Arg Val Val Asp Ser Val Gly Gly Leu
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Designed peptide

<400> SEQUENCE: 134

Ile Arg Val Val Tyr Ser Val His Met Ala
1               5                   10

<210> SEQ ID NO 135
```

```
<211> LENGTH: 10
<212> TYPE: PRT
<213> ORGANISM: Artificial Sequence
<220> FEATURE:
<223> OTHER INFORMATION: Designed peptide

<400> SEQUENCE: 135

Ile Arg Val Val Tyr Ser Val His Met Gly
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Designed peptide

<400> SEQUENCE: 136

Ile Arg Val Val Tyr Ser Val Pro Met Ala
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Designed peptide

<400> SEQUENCE: 137

Ile Arg Phe Val Gly Ser Val Cys Arg Arg
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Designed peptide

<400> SEQUENCE: 138

Ile Arg Val Val Tyr Ser Val His Met Asp
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Designed peptide

<400> SEQUENCE: 139

Val Leu Trp His Leu Val Phe Ser Asp Arg
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Designed peptide

<400> SEQUENCE: 140

Val Leu Trp His Leu Val Cys Arg Asp Arg
1               5                   10

<210> SEQ ID NO 141
<211> LENGTH: 10
```

```
<212> TYPE: PRT
<213> ORGANISM: Artificial Sequence
<220> FEATURE:
<223> OTHER INFORMATION: Designed peptide

<400> SEQUENCE: 141

Val Leu Trp Asn Val Val Tyr Ser Asp Arg
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Designed peptide

<400> SEQUENCE: 142

Val Leu Trp Asn Leu Val Phe Ser Asp Arg
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Designed peptide

<400> SEQUENCE: 143

Val Leu Trp His Leu Val Trp Ser Glu Arg
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Designed peptide

<400> SEQUENCE: 144

Val Leu Trp His Leu Val Val Ser Glu Arg
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Designed peptide

<400> SEQUENCE: 145

Val Leu Trp His Leu Val Val Ser Asp Arg
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Designed peptide

<400> SEQUENCE: 146

Val Met Trp His Leu Val Phe Ser Asp Arg
1               5                   10

<210> SEQ ID NO 147
<211> LENGTH: 10
<212> TYPE: PRT
```

```
<213> ORGANISM: Artificial Sequence
<220> FEATURE:
<223> OTHER INFORMATION: Designed peptide

<400> SEQUENCE: 147

Val Pro Val Met Gly Tyr Ile His Val Gly
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Designed peptide

<400> SEQUENCE: 148

Val Pro Phe Met Gly Tyr Ile His Val Gly
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Designed peptide

<400> SEQUENCE: 149

Val His Val Met Gly Tyr Ile His Val Gly
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Designed peptide

<400> SEQUENCE: 150

Val Thr Val Met Gly Tyr Ile His Val Gly
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Designed peptide

<400> SEQUENCE: 151

Val Pro Val Arg Gly Ser Ile Arg Val Gly
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Designed peptide

<400> SEQUENCE: 152

Val Pro Val Met Gly Tyr Ile Leu Val Gly
1               5                   10

<210> SEQ ID NO 153
<211> LENGTH: 10
<212> TYPE: PRT
<213> ORGANISM: Artificial Sequence
```

```
<220> FEATURE:
<223> OTHER INFORMATION: Designed peptide

<400> SEQUENCE: 153

Gly Pro Val Met Gly Tyr Ser His Val Gly
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Designed peptide

<400> SEQUENCE: 154

Val Pro Val Arg Gly Tyr Val Phe Val Gly
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Designed peptide

<400> SEQUENCE: 155

Asp Phe Thr Ala Arg Asp Cys Val Ala Phe
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Designed peptide

<400> SEQUENCE: 156

Asp Phe Thr Ala Arg Asp Cys Val Ala Cys
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Designed peptide

<400> SEQUENCE: 157

Asp Phe Thr Ala Arg Glu Cys Val Ala Phe
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Designed peptide

<400> SEQUENCE: 158

Asp Phe Ala Val Trp Asp Cys Val Ala Phe
1               5                   10

<210> SEQ ID NO 159
<211> LENGTH: 10
<212> TYPE: PRT
<213> ORGANISM: Artificial Sequence
<220> FEATURE:
```

<223> OTHER INFORMATION: Designed peptide

<400> SEQUENCE: 159

Asp Ile Asn Ala Arg Asn Cys Val Ala Phe
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Designed peptide

<400> SEQUENCE: 160

Asp Phe Thr Ala Arg Val Cys Val Ala Phe
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Designed peptide

<400> SEQUENCE: 161

Asp Phe Thr Gly Arg Asp Cys Val Ala Phe
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Designed peptide

<400> SEQUENCE: 162

Asp Phe Thr Ala Arg Asp Tyr Val Ala Phe
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Designed peptide

<400> SEQUENCE: 163

Asp Phe Thr Ala Trp Asp Cys Val Ala Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Designed peptide

<400> SEQUENCE: 164

Cys Val Trp Arg Arg Arg Asn Gly Leu Tyr
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Designed peptide

<400> SEQUENCE: 165

Phe Val Trp Arg Arg Arg His Cys Leu Tyr
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Designed peptide

<400> SEQUENCE: 166

Phe Val Trp Arg Arg Arg Thr Gly Leu Ser
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Designed peptide

<400> SEQUENCE: 167

Phe Val Trp Arg Arg Arg Ala Gly Leu Tyr
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Designed peptide

<400> SEQUENCE: 168

Phe Gly Trp Arg Arg Arg Ala Gly Leu Tyr
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Designed peptide

<400> SEQUENCE: 169

Phe Val Trp Arg Arg Arg Pro Gly Leu Ser
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Designed peptide

<400> SEQUENCE: 170

Cys Val Trp Arg Arg Arg Thr Gly Leu Ser
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Designed peptide

<400> SEQUENCE: 171

Phe Val Trp Arg Arg Arg Ser Gly Leu Phe
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Designed peptide

<400> SEQUENCE: 172

Ser Val Trp Arg Arg Arg Thr Gly Leu Tyr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Designed peptide

<400> SEQUENCE: 173

Ser Ser Ile Val Ser Leu Ala Gly Asp Leu
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Designed peptide

<400> SEQUENCE: 174

Ser Ser Ile Val Ser Leu Ala Gly Glu Val
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Designed peptide

<400> SEQUENCE: 175

Ser Arg Ile Val Ser Arg Ala Gly Asp Leu
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Designed peptide

<400> SEQUENCE: 176

Ser Ser Ile Val Ser Leu Ser Gly Asp Leu
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Designed peptide

<400> SEQUENCE: 177

Ser Ser Ile Val Ser Leu Ala Gly Asn Leu
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Designed peptide

<400> SEQUENCE: 178

Ser Ser Ile Val Ser Leu Ala Gly Asp Arg
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Designed peptide

<400> SEQUENCE: 179

Ser Ser Ile Val Cys Leu Ala Gly Asp Leu
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Designed peptide

<400> SEQUENCE: 180

Ser Ser Ile Val Ser Leu Ala Gly Tyr Leu
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Designed peptide

<400> SEQUENCE: 181

Ser Arg Ile Gly Ser Leu Ala Gly Asp Leu
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Designed peptide

<400> SEQUENCE: 182

Ser Ser Ile Val Ser Arg Ala Gly Asp Leu
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Designed peptide

<400> SEQUENCE: 183

```
Ser Ser Ile Val Ser Ile Ala Gly Asp Leu
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Designed peptide

<400> SEQUENCE: 184

Ser Ser Val Val Ser Leu Ala Gly Asp Phe
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Designed peptide

<400> SEQUENCE: 185

Ser Ser Ile Val Ser Leu Ala Gly Glu Leu
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Designed peptide

<400> SEQUENCE: 186

Ser Ser Leu Val Ser Leu Ala Cys Ala Leu
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Designed peptide

<400> SEQUENCE: 187

Ser Ser Ile Val Ser Leu Ala Asp Asp Leu
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Designed peptide

<400> SEQUENCE: 188

Ser Ser Ile Val Ser Leu Ala Gly Asp Val
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Designed peptide

<400> SEQUENCE: 189

Ser Arg Ile Val Ser Leu Ala Gly Asp Leu
```

```
1               5                   10
```

<210> SEQ ID NO 190
<211> LENGTH: 10
<212> TYPE: PRT
<213> ORGANISM: Artificial Sequence
<220> FEATURE:
<223> OTHER INFORMATION: Designed peptide

<400> SEQUENCE: 190

```
Ser Ser Ile Val Ser Val Ala Gly Asp Leu
1               5                   10
```

<210> SEQ ID NO 191
<211> LENGTH: 10
<212> TYPE: PRT
<213> ORGANISM: Artificial Sequence
<220> FEATURE:
<223> OTHER INFORMATION: Designed peptide

<400> SEQUENCE: 191

```
Ser Cys Ile Val Ser Leu Ala Gly Asp Leu
1               5                   10
```

<210> SEQ ID NO 192
<211> LENGTH: 10
<212> TYPE: PRT
<213> ORGANISM: Artificial Sequence
<220> FEATURE:
<223> OTHER INFORMATION: Designed peptide

<400> SEQUENCE: 192

```
Ser Ser Val Val Cys Leu Ala Gly Glu Leu
1               5                   10
```

<210> SEQ ID NO 193
<211> LENGTH: 10
<212> TYPE: PRT
<213> ORGANISM: Artificial Sequence
<220> FEATURE:
<223> OTHER INFORMATION: Designed peptide

<400> SEQUENCE: 193

```
Ser Ser Ile Val Ser Phe Ala Gly Asp Phe
1               5                   10
```

<210> SEQ ID NO 194
<211> LENGTH: 10
<212> TYPE: PRT
<213> ORGANISM: Artificial Sequence
<220> FEATURE:
<223> OTHER INFORMATION: Designed peptide

<400> SEQUENCE: 194

```
Ser Ser Val Val Ser Leu Ala Gly Asp Leu
1               5                   10
```

<210> SEQ ID NO 195
<211> LENGTH: 10
<212> TYPE: PRT
<213> ORGANISM: Artificial Sequence
<220> FEATURE:
<223> OTHER INFORMATION: Designed peptide

<400> SEQUENCE: 195

```
Ser Ser Met Val Ser Leu Ala Gly Asp Leu
1               5                   10
```

<210> SEQ ID NO 196
<211> LENGTH: 10
<212> TYPE: PRT
<213> ORGANISM: Artificial Sequence
<220> FEATURE:
<223> OTHER INFORMATION: Designed peptide

<400> SEQUENCE: 196

Ser Arg Ser Val Ser Leu Ala Gly Asp Arg
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Designed peptide

<400> SEQUENCE: 197

Ser Ser Met Val Ser Phe Ala Gly Asp Leu
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Designed peptide

<400> SEQUENCE: 198

Arg Ser Ile Val Ser Leu Ala Gly Asp Leu
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Designed peptide

<400> SEQUENCE: 199

Ser Ser Ile Val Ser Leu Val Gly Asp Leu
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Designed peptide

<400> SEQUENCE: 200

Ser Ser Ile Val Ser Leu Glu Gly Asp Leu
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Designed peptide

<400> SEQUENCE: 201

Ser Ser Ile Val Ser Leu Ala Gly Gly Leu
1               5                   10

```
<210> SEQ ID NO 202
<211> LENGTH: 10
<212> TYPE: PRT
<213> ORGANISM: Artificial Sequence
<220> FEATURE:
<223> OTHER INFORMATION: Designed peptide

<400> SEQUENCE: 202

Ser Ser Ile Val Ser Leu Leu Gly Asp Leu
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Designed peptide

<400> SEQUENCE: 203

Ser Ser Ile Val Ser Leu Ala Gly Ala Leu
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Designed peptide

<400> SEQUENCE: 204

Gly Ser Ile Val Ser Leu Ala Gly Asp Leu
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Designed peptide

<400> SEQUENCE: 205

Phe Val Trp Ser Arg Arg Thr Gly Leu Tyr
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Designed peptide

<400> SEQUENCE: 206

Phe Val Trp Ser Arg Gln Thr Gly Leu Tyr
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Designed peptide

<400> SEQUENCE: 207

Phe Val Trp Ser Arg Arg Thr Gly Ile Tyr
1               5                   10
```

```
<210> SEQ ID NO 208
<211> LENGTH: 10
<212> TYPE: PRT
<213> ORGANISM: Artificial Sequence
<220> FEATURE:
<223> OTHER INFORMATION: Designed peptide

<400> SEQUENCE: 208

Phe Val Trp Ser Leu Leu Thr Val Leu Tyr
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Designed peptide

<400> SEQUENCE: 209

Phe Val Trp Ser Arg Arg Ala Gly Leu Tyr
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Designed peptide

<400> SEQUENCE: 210

Phe Val Trp Ser Arg Arg Ile Gly Val Tyr
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Designed peptide

<400> SEQUENCE: 211

Phe Val Trp Asn Arg Arg Thr Gly Leu Tyr
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Designed peptide

<400> SEQUENCE: 212

Phe Val Trp Ser Arg Arg Asn Gly Leu Tyr
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Designed peptide

<400> SEQUENCE: 213

Phe Val Trp Arg Arg Arg Thr Gly Leu Tyr
1               5                   10

<210> SEQ ID NO 214
```

```
<211> LENGTH: 10
<212> TYPE: PRT
<213> ORGANISM: Artificial Sequence
<220> FEATURE:
<223> OTHER INFORMATION: Designed peptide

<400> SEQUENCE: 214

Leu Val Trp Ser Arg Arg Thr Gly Leu Tyr
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Designed peptide

<400> SEQUENCE: 215

Phe Val Leu Ser Arg Arg Thr Cys Ile Tyr
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Designed peptide

<400> SEQUENCE: 216

Phe Val Trp Ser Lys Arg Thr Gly Leu Tyr
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Designed peptide

<400> SEQUENCE: 217

Phe Val Trp Ser Arg Arg Pro Gly Leu Tyr
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Designed peptide

<400> SEQUENCE: 218

Phe Val Trp Ser Arg Arg Ser Gly Leu Tyr
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Designed peptide

<400> SEQUENCE: 219

Phe Val Trp Ser Arg Trp Thr Gly Leu Tyr
1               5                   10

<210> SEQ ID NO 220
<211> LENGTH: 10
```

<212> TYPE: PRT
<213> ORGANISM: Artificial Sequence
<220> FEATURE:
<223> OTHER INFORMATION: Designed peptide

<400> SEQUENCE: 220

Phe Val Trp Ser Arg Gln Thr Ser Leu Tyr
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Designed peptide

<400> SEQUENCE: 221

Phe Val Trp Ser Arg Arg Thr Gly Leu Asp
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Designed peptide

<400> SEQUENCE: 222

Phe Val Trp Ser Arg Arg Thr Gly Arg Tyr
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Designed peptide

<400> SEQUENCE: 223

Val Val Trp Ser Arg Arg Thr Gly Leu Tyr
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Designed peptide

<400> SEQUENCE: 224

Phe Val Gly Ser Arg Arg Thr Gly Leu Tyr
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Designed peptide

<400> SEQUENCE: 225

Phe Val Trp Ser Arg Arg Thr Ser Leu Tyr
1               5                   10

<210> SEQ ID NO 226
<211> LENGTH: 10
<212> TYPE: PRT

```
<213> ORGANISM: Artificial Sequence
<220> FEATURE:
<223> OTHER INFORMATION: Designed peptide

<400> SEQUENCE: 226

Phe Phe Trp Ser Met Arg Thr Gly Leu Tyr
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Designed peptide

<400> SEQUENCE: 227

Phe Val Trp Ser Arg Arg Thr Gly Leu Phe
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Designed peptide

<400> SEQUENCE: 228

Phe Val Trp Ser Gly Arg Ile Gly Val Tyr
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Designed peptide

<400> SEQUENCE: 229

Phe Val Trp Ser Arg Arg Thr Gly Ile Phe
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Designed peptide

<400> SEQUENCE: 230

Phe Val Trp Ser Arg Arg Thr Gly Leu Ser
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Designed peptide

<400> SEQUENCE: 231

Phe Val Trp Ser Arg Arg Thr Val Ile Leu
1               5                   10

<210> SEQ ID NO 232
<211> LENGTH: 10
<212> TYPE: PRT
<213> ORGANISM: Artificial Sequence
```

```
<220> FEATURE:
<223> OTHER INFORMATION: Designed peptide

<400> SEQUENCE: 232

Phe Val Trp Ser Arg Arg Thr Val Leu Leu
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Designed peptide

<400> SEQUENCE: 233

Val Val Trp Ser Arg Arg Thr Gly Arg Tyr
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Designed peptide

<400> SEQUENCE: 234

Phe Val Trp Cys Arg Arg Thr Gly Leu Tyr
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Designed peptide

<400> SEQUENCE: 235

Phe Val Trp Ser Arg Arg Thr Gly Phe Tyr
1               5                   10

<210> SEQ ID NO 236
<211> LENGTH: 10
<212> TYPE: PRT
<213> ORGANISM: Artificial Sequence
<220> FEATURE:
<223> OTHER INFORMATION: Designed peptide

<400> SEQUENCE: 236

Phe Val Trp Cys Arg Trp Thr Gly Leu Tyr
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Designed peptide

<400> SEQUENCE: 237

Phe Val Trp Ser Arg Arg Thr Asp Leu Tyr
1               5                   10

<210> SEQ ID NO 238
<211> LENGTH: 10
<212> TYPE: PRT
<213> ORGANISM: Artificial Sequence
<220> FEATURE:
```

```
<223> OTHER INFORMATION: Designed peptide

<400> SEQUENCE: 238

Phe Val Trp Ser Arg Arg Thr Val Leu Tyr
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Designed peptide

<400> SEQUENCE: 239

Phe Val Trp Ser Trp Arg Thr Gly Leu Tyr
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Designed peptide

<400> SEQUENCE: 240

Phe Val Trp Cys Arg Arg Thr Gly Ile Tyr
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Designed peptide

<400> SEQUENCE: 241

Phe Val Trp Ser Met Arg Thr Gly Leu Tyr
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Designed peptide

<400> SEQUENCE: 242

Phe Val Trp Ser Arg Arg Thr Gly Val Cys
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Designed peptide

<400> SEQUENCE: 243

Phe Val Trp Ser Trp Arg Ile Gly Leu Tyr
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Designed peptide
```

<400> SEQUENCE: 244

Phe Val Trp Ser Arg Gln Thr Gly Val Tyr
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Designed peptide

<400> SEQUENCE: 245

Phe Val Trp Ser Arg Arg Ile Gly Leu Tyr
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Designed peptide

<400> SEQUENCE: 246

Phe Val Trp Ser Arg Arg Thr Cys Leu Tyr
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Designed peptide

<400> SEQUENCE: 247

Phe Val Trp Ser Arg Arg Thr Gly Ser Tyr
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Designed peptide

<400> SEQUENCE: 248

Phe Val Trp Ser Arg Arg Ser Gly Ile Tyr
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Designed peptide

<400> SEQUENCE: 249

Phe Val Trp Ser Arg Arg Thr Gly Val Tyr
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Designed peptide

```
<400> SEQUENCE: 250

Phe Phe Trp Ser Arg Arg Thr Cys Ile Tyr
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Designed peptide

<400> SEQUENCE: 251

Phe Val Leu Ser Arg Arg Thr Gly Leu Tyr
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Designed peptide

<400> SEQUENCE: 252

Phe Val Trp Ser Gly Arg Thr Gly Leu Tyr
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Designed peptide

<400> SEQUENCE: 253

Phe Val Trp Ser Trp Arg Ser Gly Leu Tyr
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Designed peptide

<400> SEQUENCE: 254

Phe Val Trp Ser Arg Arg Thr Val Leu Phe
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Designed peptide

<400> SEQUENCE: 255

Phe Val Trp Ser Arg Trp Ala Gly Leu Tyr
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Designed peptide

<400> SEQUENCE: 256
```

Phe Gly Trp Ser Met Arg Thr Gly Leu Tyr
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Designed peptide

<400> SEQUENCE: 257

Phe Val Trp Gly Arg Arg Thr Gly Leu Tyr
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Designed peptide

<400> SEQUENCE: 258

Phe Val Trp Ser Arg Arg Thr Gly Leu Cys
1               5                   10

<210> SEQ ID NO 259
<211> LENGTH: 10
<212> TYPE: PRT
<213> ORGANISM: Artificial Sequence
<220> FEATURE:
<223> OTHER INFORMATION: Designed peptide

<400> SEQUENCE: 259

Phe Val Trp Arg Arg Arg Thr Ser Leu Tyr
1               5                   10

<210> SEQ ID NO 260
<211> LENGTH: 10
<212> TYPE: PRT
<213> ORGANISM: Artificial Sequence
<220> FEATURE:
<223> OTHER INFORMATION: Designed peptide

<400> SEQUENCE: 260

Phe Val Trp Ser Arg Trp Thr Gly Leu Cys
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Designed peptide

<400> SEQUENCE: 261

Glu Asn Tyr Arg Trp Ser Arg Ser Ile Lys
1               5                   10

<210> SEQ ID NO 262
<211> LENGTH: 10
<212> TYPE: PRT
<213> ORGANISM: Artificial Sequence
<220> FEATURE:
<223> OTHER INFORMATION: Designed peptide

<400> SEQUENCE: 262

Asp Asn Tyr Arg Trp Ser Arg Ser Ile Lys
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Designed peptide

<400> SEQUENCE: 263

Ala Asn Tyr Arg Trp Ser Arg Ser Ile Lys
1               5                   10

<210> SEQ ID NO 264
<211> LENGTH: 10
<212> TYPE: PRT
<213> ORGANISM: Artificial Sequence
<220> FEATURE:
<223> OTHER INFORMATION: Designed peptide

<400> SEQUENCE: 264

Thr Ala Gln Arg Leu Gln Trp Glu Asn Arg
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Designed peptide

<400> SEQUENCE: 265

Thr Glu Gln Arg Leu Gln Trp Glu Asn Arg
1               5                   10

<210> SEQ ID NO 266
<211> LENGTH: 10
<212> TYPE: PRT
<213> ORGANISM: Artificial Sequence
<220> FEATURE:
<223> OTHER INFORMATION: Designed peptide

<400> SEQUENCE: 266

Thr Tyr Gln Arg Leu Gln Trp Glu Asn Arg
1               5                   10

<210> SEQ ID NO 267
<211> LENGTH: 10
<212> TYPE: PRT
<213> ORGANISM: Artificial Sequence
<220> FEATURE:
<223> OTHER INFORMATION: Designed peptide

<400> SEQUENCE: 267

Ile Gly Cys Ile Val Ser Gly Ser Asn Asn
1               5                   10

<210> SEQ ID NO 268
<211> LENGTH: 10
<212> TYPE: PRT
<213> ORGANISM: Artificial Sequence
<220> FEATURE:
<223> OTHER INFORMATION: Designed peptide

<400> SEQUENCE: 268

Ile Gly Cys Ile Val Ser Gly Ser Asn Thr

```
<210> SEQ ID NO 269
<211> LENGTH: 10
<212> TYPE: PRT
<213> ORGANISM: Artificial Sequence
<220> FEATURE:
<223> OTHER INFORMATION: Designed peptide

<400> SEQUENCE: 269

Ile Gly Cys Ile Val Ser Gly Ser Thr Asn
1               5                   10

<210> SEQ ID NO 270
<211> LENGTH: 10
<212> TYPE: PRT
<213> ORGANISM: Artificial Sequence
<220> FEATURE:
<223> OTHER INFORMATION: Designed peptide

<400> SEQUENCE: 270

Thr Phe Ser Met Asn Thr His Arg Gly Ala
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Designed peptide

<400> SEQUENCE: 271

Thr Phe Ser Met Asn Thr His Arg Gly Val
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Designed peptide

<400> SEQUENCE: 272

Asn Phe Ser Met Asn Thr His Arg Gly Ala
1               5                   10

<210> SEQ ID NO 273
<211> LENGTH: 10
<212> TYPE: PRT
<213> ORGANISM: Artificial Sequence
<220> FEATURE:
<223> OTHER INFORMATION: Designed peptide

<400> SEQUENCE: 273

Ser Asn Thr Arg Gly Asn Met Asp Asp Ser
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Designed peptide

<400> SEQUENCE: 274

Ser Asn Thr Arg Gly Asn Met Asp Asp Tyr
1               5                   10
```

```
<210> SEQ ID NO 275
<211> LENGTH: 10
<212> TYPE: PRT
<213> ORGANISM: Artificial Sequence
<220> FEATURE:
<223> OTHER INFORMATION: Designed peptide

<400> SEQUENCE: 275

Ser Asn Thr Arg Gly Asn Met Asp Asp Phe
1               5                   10

<210> SEQ ID NO 276
<211> LENGTH: 10
<212> TYPE: PRT
<213> ORGANISM: Artificial Sequence
<220> FEATURE:
<223> OTHER INFORMATION: Designed peptide

<400> SEQUENCE: 276

Gln Thr Gly His Leu Asn Ser Arg His Tyr
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Designed peptide

<400> SEQUENCE: 277

Gln Thr Gly His Leu Asn Ser Arg His Asp
1               5                   10

<210> SEQ ID NO 278
<211> LENGTH: 10
<212> TYPE: PRT
<213> ORGANISM: Artificial Sequence
<220> FEATURE:
<223> OTHER INFORMATION: Designed peptide

<400> SEQUENCE: 278

Pro Thr Gly His Leu Asn Ser Arg His Asp
1               5                   10

<210> SEQ ID NO 279
<211> LENGTH: 10
<212> TYPE: PRT
<213> ORGANISM: Artificial Sequence
<220> FEATURE:
<223> OTHER INFORMATION: Designed peptide

<400> SEQUENCE: 279

Ile Thr Gln Met Asn Arg Val Val Glu Lys
1               5                   10

<210> SEQ ID NO 280
<211> LENGTH: 10
<212> TYPE: PRT
<213> ORGANISM: Artificial Sequence
<220> FEATURE:
<223> OTHER INFORMATION: Designed peptide

<400> SEQUENCE: 280

Ile Ser Gln Met Asn Arg Val Val Glu Lys
1               5                   10
```

<210> SEQ ID NO 281
<211> LENGTH: 10
<212> TYPE: PRT
<213> ORGANISM: Artificial Sequence
<220> FEATURE:
<223> OTHER INFORMATION: Designed peptide

<400> SEQUENCE: 281

Ile Asn Gln Met Asn Arg Val Val Glu Lys
1               5                   10

<210> SEQ ID NO 282
<211> LENGTH: 10
<212> TYPE: PRT
<213> ORGANISM: Artificial Sequence
<220> FEATURE:
<223> OTHER INFORMATION: Designed peptide

<400> SEQUENCE: 282

Arg Ser Met Ser Leu His Val Ser Met Ile
1               5                   10

<210> SEQ ID NO 283
<211> LENGTH: 10
<212> TYPE: PRT
<213> ORGANISM: Artificial Sequence
<220> FEATURE:
<223> OTHER INFORMATION: Designed peptide

<400> SEQUENCE: 283

Arg Ser Met Ser Leu His Val Ser Met Thr
1               5                   10

<210> SEQ ID NO 284
<211> LENGTH: 10
<212> TYPE: PRT
<213> ORGANISM: Artificial Sequence
<220> FEATURE:
<223> OTHER INFORMATION: Designed peptide

<400> SEQUENCE: 284

Arg Ser Met Ser Leu His Val Ser Met Arg
1               5                   10

<210> SEQ ID NO 285
<211> LENGTH: 10
<212> TYPE: PRT
<213> ORGANISM: Artificial Sequence
<220> FEATURE:
<223> OTHER INFORMATION: Designed peptide

<400> SEQUENCE: 285

Gln Val Leu Gly Gln Asn Glu His Glu Asp
1               5                   10

<210> SEQ ID NO 286
<211> LENGTH: 10
<212> TYPE: PRT
<213> ORGANISM: Artificial Sequence
<220> FEATURE:
<223> OTHER INFORMATION: Designed peptide

<400> SEQUENCE: 286

Gln Val Leu Gly Gln Asn Glu His Glu Phe
1               5                   10

```
<210> SEQ ID NO 287
<211> LENGTH: 10
<212> TYPE: PRT
<213> ORGANISM: Artificial Sequence
<220> FEATURE:
<223> OTHER INFORMATION: Designed peptide

<400> SEQUENCE: 287

Gln Val Leu Gly Gln Asn Glu His Glu Tyr
1               5                   10

<210> SEQ ID NO 288
<211> LENGTH: 10
<212> TYPE: PRT
<213> ORGANISM: Artificial Sequence
<220> FEATURE:
<223> OTHER INFORMATION: Designed peptide

<400> SEQUENCE: 288

Cys Lys Ala Arg Ser Ala Arg Gly Val Ser
1               5                   10

<210> SEQ ID NO 289
<211> LENGTH: 10
<212> TYPE: PRT
<213> ORGANISM: Artificial Sequence
<220> FEATURE:
<223> OTHER INFORMATION: Designed peptide

<400> SEQUENCE: 289

Cys Thr Ala Arg Ser Ala Arg Gly Val Ser
1               5                   10

<210> SEQ ID NO 290
<211> LENGTH: 10
<212> TYPE: PRT
<213> ORGANISM: Artificial Sequence
<220> FEATURE:
<223> OTHER INFORMATION: Designed peptide

<400> SEQUENCE: 290

Gly Lys Ala Arg Ser Ala Arg Gly Val Ser
1               5                   10

<210> SEQ ID NO 291
<211> LENGTH: 10
<212> TYPE: PRT
<213> ORGANISM: Artificial Sequence
<220> FEATURE:
<223> OTHER INFORMATION: Designed peptide

<400> SEQUENCE: 291

Ile Val Met Thr Pro Asn Ala Lys Asp His
1               5                   10

<210> SEQ ID NO 292
<211> LENGTH: 10
<212> TYPE: PRT
<213> ORGANISM: Artificial Sequence
<220> FEATURE:
<223> OTHER INFORMATION: Designed peptide

<400> SEQUENCE: 292

Ile Val Met Thr Pro Asn Ala Lys Tyr His
1               5                   10

<210> SEQ ID NO 293
```

```
<211> LENGTH: 10
<212> TYPE: PRT
<213> ORGANISM: Artificial Sequence
<220> FEATURE:
<223> OTHER INFORMATION: Designed peptide

<400> SEQUENCE: 293

Ile Val Met Thr Pro Asn Ala Lys Tyr Pro
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Designed peptide

<400> SEQUENCE: 294

Ala Asn Ile Asp Phe Asn His Tyr Gly Ala
1               5                   10

<210> SEQ ID NO 295
<211> LENGTH: 10
<212> TYPE: PRT
<213> ORGANISM: Artificial Sequence
<220> FEATURE:
<223> OTHER INFORMATION: Designed peptide

<400> SEQUENCE: 295

Glu Asn Ile Asp Phe Asn His Tyr Gly Ala
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Designed peptide

<400> SEQUENCE: 296

Glu Asn Ile Asp Phe Asn His Tyr Gly Val
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Designed peptide

<400> SEQUENCE: 297

Lys Ala Lys Leu Thr Glu His Ser His His
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Designed peptide

<400> SEQUENCE: 298

Lys Ala Lys Leu Thr Glu His Ser Pro His
1               5                   10

<210> SEQ ID NO 299
<211> LENGTH: 10
```

```
<212> TYPE: PRT
<213> ORGANISM: Artificial Sequence
<220> FEATURE:
<223> OTHER INFORMATION: Designed peptide

<400> SEQUENCE: 299

Lys Ala Lys Leu Thr Glu His Ser His Pro
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Designed peptide

<400> SEQUENCE: 300

Phe Val Trp Cys Arg Arg Thr Gly Leu Cys
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Designed peptide

<400> SEQUENCE: 301

Lys Ser Leu Leu Asp Ala Arg Asp Asn Ser
1               5                   10

<210> SEQ ID NO 302
<211> LENGTH: 10
<212> TYPE: PRT
<213> ORGANISM: Artificial Sequence
<220> FEATURE:
<223> OTHER INFORMATION: Designed peptide

<400> SEQUENCE: 302

Val Trp Trp Gly Arg Arg Ile Ser Arg Phe
1               5                   10

<210> SEQ ID NO 303
<211> LENGTH: 10
<212> TYPE: PRT
<213> ORGANISM: Artificial Sequence
<220> FEATURE:
<223> OTHER INFORMATION: Designed peptide

<400> SEQUENCE: 303

Ile Ser Asn Val Arg Gly Ser Tyr Val Asp
1               5                   10

<210> SEQ ID NO 304
<211> LENGTH: 10
<212> TYPE: PRT
<213> ORGANISM: Artificial Sequence
<220> FEATURE:
<223> OTHER INFORMATION: Designed peptide

<400> SEQUENCE: 304

Arg Arg Gly Val Cys Ser Gly Pro Gly Val
1               5                   10

<210> SEQ ID NO 305
<211> LENGTH: 10
<212> TYPE: PRT
```

```
<213> ORGANISM: Artificial Sequence
<220> FEATURE:
<223> OTHER INFORMATION: Designed peptide

<400> SEQUENCE: 305

Ile Lys Arg Asp Phe Cys Gly Cys Tyr Arg
1               5                   10

<210> SEQ ID NO 306
<211> LENGTH: 10
<212> TYPE: PRT
<213> ORGANISM: Artificial Sequence
<220> FEATURE:
<223> OTHER INFORMATION: Designed peptide

<400> SEQUENCE: 306

Val Leu Thr Ser Val Pro Glu Leu Arg Gly
1               5                   10

<210> SEQ ID NO 307
<211> LENGTH: 10
<212> TYPE: PRT
<213> ORGANISM: Artificial Sequence
<220> FEATURE:
<223> OTHER INFORMATION: Designed peptide

<400> SEQUENCE: 307

Met Ile Asp Ser Arg Ile Pro Arg Glu Phe
1               5                   10

<210> SEQ ID NO 308
<211> LENGTH: 10
<212> TYPE: PRT
<213> ORGANISM: Artificial Sequence
<220> FEATURE:
<223> OTHER INFORMATION: Designed peptide

<400> SEQUENCE: 308

Leu Ile Leu Arg Val Phe Gly Arg Trp Gly
1               5                   10

<210> SEQ ID NO 309
<211> LENGTH: 10
<212> TYPE: PRT
<213> ORGANISM: Artificial Sequence
<220> FEATURE:
<223> OTHER INFORMATION: Designed peptide

<400> SEQUENCE: 309

Val Phe Phe Val Ser Ser Arg Asn Arg Ala
1               5                   10

<210> SEQ ID NO 310
<211> LENGTH: 10
<212> TYPE: PRT
<213> ORGANISM: Artificial Sequence
<220> FEATURE:
<223> OTHER INFORMATION: Designed peptide

<400> SEQUENCE: 310

Val Ile Ser Phe Gly Gly Arg Arg Phe Gly
1               5                   10

<210> SEQ ID NO 311
<211> LENGTH: 10
<212> TYPE: PRT
<213> ORGANISM: Artificial Sequence
```

<220> FEATURE:
<223> OTHER INFORMATION: Designed peptide

<400> SEQUENCE: 311

Ser Val Ser Thr Met Ser Ala Phe Cys Leu
1               5                   10

<210> SEQ ID NO 312
<211> LENGTH: 10
<212> TYPE: PRT
<213> ORGANISM: Artificial Sequence
<220> FEATURE:
<223> OTHER INFORMATION: Designed peptide

<400> SEQUENCE: 312

Lys Asn Leu Lys Lys His Thr Gly Asn Thr
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Designed peptide

<400> SEQUENCE: 313

Gly Val Gly Leu Asn Ser Val Asp Arg Asp
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Designed peptide

<400> SEQUENCE: 314

Asp Pro Arg Ile Ser Thr Gly Asn Val Phe
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Designed peptide

<400> SEQUENCE: 315

Val Ala Ile Asp Ile Ser Ile Arg Met Arg
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Designed peptide

<400> SEQUENCE: 316

Val Ser Phe Ser Cys His Ala Cys Ser Thr
1               5                   10

<210> SEQ ID NO 317
<211> LENGTH: 10
<212> TYPE: PRT
<213> ORGANISM: Artificial Sequence
<220> FEATURE:

<223> OTHER INFORMATION: Designed peptide

<400> SEQUENCE: 317

Tyr Leu Ser Cys Asp Tyr Val Phe Cys Gly
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Designed peptide

<400> SEQUENCE: 318

Thr Asp Thr Leu His Ser Ile Lys Leu Val
1               5                   10

<210> SEQ ID NO 319
<211> LENGTH: 10
<212> TYPE: PRT
<213> ORGANISM: Artificial Sequence
<220> FEATURE:
<223> OTHER INFORMATION: Designed peptide

<400> SEQUENCE: 319

Ser Thr Gly Pro Val Val Asn Thr Gln Tyr
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Designed peptide

<400> SEQUENCE: 320

Ser Leu Thr Ser Met Thr His Ser Thr Lys
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Designed peptide

<400> SEQUENCE: 321

Thr Leu Ser Asn Asp Thr Gly Asp Leu Thr
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Designed peptide

<400> SEQUENCE: 322

Ser Arg Gly Phe Ser Met Lys Arg Pro Ala
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Designed peptide

<400> SEQUENCE: 323

Gly Val Gly Cys Ile Met Ser Ser Ile Gly
1               5                   10

<210> SEQ ID NO 324
<211> LENGTH: 10
<212> TYPE: PRT
<213> ORGANISM: Artificial Sequence
<220> FEATURE:
<223> OTHER INFORMATION: Designed peptide

<400> SEQUENCE: 324

Ser Met Ser Cys Val Asp Ser Thr Ser Val
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Designed peptide

<400> SEQUENCE: 325

Arg Ser Asn Thr Lys Ile Met Met Val Asn
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Designed peptide

<400> SEQUENCE: 326

Ile Gln Arg Thr Arg Thr Asp Gln Ala Asn
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Designed peptide

<400> SEQUENCE: 327

Gly Glu Phe Ser Cys Val Ile Ala Ser Val
1               5                   10

<210> SEQ ID NO 328
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 328
cagacgtgtg ctcttccgat ctgatatcag atcggaagag cgtcgttaag         50

<210> SEQ ID NO 329
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 329
catcacaagt ttgtacaaaa aagcaggctg tga         33

<210> SEQ ID NO 330
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 330
tatcaccact ttgtacaaga aagctgggtt             30

<210> SEQ ID NO 331
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 331
atcacaagtt tgtactggga gggcgatcgc a           31

<210> SEQ ID NO 332
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 332
ctatcaccac tttgttcgct acctcgcgaa             30

<210> SEQ ID NO 333
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 333
acaagtggtg atagcttgtc gagaagta               28

<210> SEQ ID NO 334
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 334
gtacaaactt gtgatgatcc gcgcccgat              29

<210> SEQ ID NO 335
<211> LENGTH: 103
<212> TYPE: DNA
<213> ORGANISM: Artificial Sequence
<220> FEATURE:
<223> OTHER INFORMATION: Synthetic oligonucleotide

<400> SEQUENCE: 335 cccaaataa tgattttatt ttgactgata gtgacctgtt cgttgcaaca aattgatgag        60
caatgctttt ttataatgcc aactttgtac aaaaaagcag gct                       103

<210> SEQ ID NO 336

```
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 336
agcttaccca gctttcttgt acaaagttgg cattataaga aagcattgct tatcaatttg      60
ttgcaacgaa caggtcacta tcagtcaaaa taaaatcatt atttg                    105

<210> SEQ ID NO 337
<211> LENGTH: 217
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (124)..(153)
<223> OTHER INFORMATION: n is a, c, g, or t

<400> SEQUENCE: 337
gatcccgcga aattaatacg actcactata ggggaagtat ttttacaaca attaccaaca      60
acaacaacaa acaacaacaa cattacattt tacattctac aactacaagc caccatgggc    120
tgcnnnnnnn nnnnnnnnnn nnnnnnnnnn nnntgcgggg gaggcagcca tcatcatcat    180
catcacggcg gaagcaggac gggggcggc gtggaaa                              217

<210> SEQ ID NO 338
<211> LENGTH: 117
<212> TYPE: DNA
<213> ORGANISM: Artificial Sequence
<220> FEATURE:
<223> OTHER INFORMATION: Synthetic oligonucleotide

<400> SEQUENCE: 338
gatcccgcga aattaatacg actcactata ggggaagtat ttttacaaca attaccaaca      60
acaacaacaa acaacaacaa cattacattt tacattctac aactacaagc caccatg       117

<210> SEQ ID NO 339
<211> LENGTH: 78
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(55)
<223> OTHER INFORMATION: n is a, c, g, or t

<400> SEQUENCE: 339
acaactacaa gccaccatgg gctgcnnnnn nnnnnnnnnn nnnnnnnnnn nnnnntgcgg      60
gggaggcagc catcatca                                                   78

<210> SEQ ID NO 340
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 340
tttccacgcc gcccccgtc ctgcttccgc cgtgatgatg atgatgatgg ctgcctcccc      60
c                                                                    61
```

<210> SEQ ID NO 341
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Biotin-TEG-dA
<220> FEATURE:
<221> NAME/KEY: misc_feature
<222> LOCATION: (3)..(3)
<223> OTHER INFORMATION: riboguanine
<220> FEATURE:
<221> NAME/KEY: misc_feature
<222> LOCATION: (12)..(12)
<223> OTHER INFORMATION: 3-Cyanovinylcarbazole-dG
<220> FEATURE:
<221> NAME/KEY: misc_feature
<222> LOCATION: (23)..(23)
<223> OTHER INFORMATION: Amino C6-dT

<400> SEQUENCE: 341
nanaatttcc anccgccccc cgncct                                26

<210> SEQ ID NO 342
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 342
gatcccgcga aattaatacg actcactata ggggaagtat ttttacaaca attaccaaca     60

<210> SEQ ID NO 343
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 343
tttccacgcc gcccccgtc ct                                     22

<210> SEQ ID NO 344
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 344
tcgtcggcag cgtcagatgt gtataagaga cagcattcta caactacaag ccaccatg      58

<210> SEQ ID NO 345
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 345
gtctcgtggg ctcggagatg tgtataagag acagtttcca cgccgccccc cgtcctgctt     60
c                                                           61

<210> SEQ ID NO 346
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 346
caagcagaag acggcatacg agatgcgtag tagtctcgtg ggctcgg          47

<210> SEQ ID NO 347
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 347
caagcagaag acggcatacg agatcggagc ctgtctcgtg ggctcgg          47

<210> SEQ ID NO 348
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 348
aatgatacgg cgaccaccga gatctacact ctctccgtcg tcggcagcgt c      51

<210> SEQ ID NO 349
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 349
aatgatacgg cgaccaccga gatctacacc gtctaattcg tcggcagcgt c      51

<210> SEQ ID NO 350
<211> LENGTH: 40
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Biotin-TEG-dA
<220> FEATURE:
<221> NAME/KEY: misc_feature
<222> LOCATION: (21)..(21)
<223> OTHER INFORMATION: deoxyinosine
<220> FEATURE:
<221> NAME/KEY: misc_feature
<222> LOCATION: (27)..(27)
<223> OTHER INFORMATION: 3-Cyanovinylcarbazole-dG
<220> FEATURE:
<221> NAME/KEY: misc_feature
<222> LOCATION: (38)..(38)
<223> OTHER INFORMATION: Amino C6-dT

<400> SEQUENCE: 350
naaaaaaaaa aaaaaaaaaa nttccanccg cccccccgnct                 40